United States Patent
Walther et al.

(10) Patent No.: US 10,556,937 B2
(45) Date of Patent: Feb. 11, 2020

(54) METHODS FOR THE PRODUCTION OF A COSMETIC COMPOSITION COMPRISING LEUKOLECTIN AND USES THEREOF

(71) Applicant: AQUA BIO TECHNOLOGY ASA, Fornebu (NO)

(72) Inventors: Bernt Th. Walther, Bergen (NO); Hans Kristian Leren, Bergen (NO); Fanny Fagot, Oslo (NO)

(73) Assignee: AQUA BIO TECHNOLOGY ASA, Bergen (NO)

( * ) Notice: Subject to any disclaimer, the term of this patent is extended or adjusted under 35 U.S.C. 154(b) by 58 days.

(21) Appl. No.: 16/010,962

(22) Filed: Jun. 18, 2018

(65) Prior Publication Data

US 2018/0298067 A1    Oct. 18, 2018

Related U.S. Application Data

(62) Division of application No. 14/128,721, filed as application No. PCT/EP2012/062252 on Jun. 25, 2012, now Pat. No. 10,017,552.

(30) Foreign Application Priority Data

Jun. 24, 2011  (GB) .................................. 1110777.8

(51) Int. Cl.
| | | |
|---|---|---|
| *A61K 8/64* | (2006.01) | |
| *A61Q 19/00* | (2006.01) | |
| *A61Q 19/08* | (2006.01) | |
| *C07K 1/34* | (2006.01) | |
| *C07K 14/46* | (2006.01) | |
| *A61K 38/17* | (2006.01) | |
| *A61Q 19/02* | (2006.01) | |

(52) U.S. Cl.
CPC .............. *C07K 14/461* (2013.01); *A61K 8/64* (2013.01); *A61K 38/1706* (2013.01); *A61Q 19/00* (2013.01); *A61Q 19/007* (2013.01); *A61Q 19/02* (2013.01); *A61Q 19/08* (2013.01); *C07K 1/34* (2013.01)

(58) Field of Classification Search
None
See application file for complete search history.

(56) References Cited

U.S. PATENT DOCUMENTS

| | | |
|---|---|---|
| 4,942,153 A | 7/1990 | Fernandez |
| 5,492,894 A | 2/1996 | Bascom |
| 6,416,769 B1 | 7/2002 | Vromen |
| 6,899,863 B1 | 5/2005 | Dhellin et al. |
| 2008/0038300 A1 | 2/2008 | Jaspers et al. |
| 2009/0043236 A1 | 2/2009 | Kawamura et al. |

FOREIGN PATENT DOCUMENTS

| | | |
|---|---|---|
| EP | 1 000 613 | 5/2000 |
| JP | 2002-535665 | 10/2002 |
| WO | 94/11497 | 5/1994 |
| WO | 99/12041 | 3/1999 |
| WO | 99/29836 | 6/1999 |
| WO | 02/19982 | 3/2002 |
| WO | 2005/067499 | 7/2005 |
| WO | 2007/059584 | 5/2007 |
| WO | 2009/085302 | 7/2009 |
| WO | 10/049688 | 5/2010 |
| WO | 11/064384 | 6/2011 |
| WO | 11/135059 | 11/2011 |

OTHER PUBLICATIONS

International Search Report and Written Opinion for PCT/EP2012/062252, dated Jun. 14, 2013.
Oppen-Berntsen, D. et al., The Effects of Hypoxia, Alkalinity and Neurochemicals on Hatching of Atlantic Salmon (*Salmo salar*) Eggs, Aquaculture, 86 (1990) 417-430.
Hayflick, L. et al., The serial cultivation of human diploid cell strains, Experimental Cell Research, 25 (1961) 585-621.
Office Action issued in corresponding Russian application No. 2014102047/15(003051) with English translation, dated Nov. 16, 2015.
Decision on Granting a Patent for Invention dated Mar. 25, 2016 in corresponding Russian Application No. 2014102047/15(003051).
Suzuki et al., "Molecular diversity of skin mucus lectins in fish", Comparative Biochemistry and Physiology Part B, 2003, vol. 136, Issue 4, pp. 723-730.
Press release for Zonase X™, by Aqua Bio Technology AS, Oslo, Norway, dated Mar. 30, 2010.
First sale of Zonase X™ by Aqua Bio Technology AS, Oslo, Norway, occurred on Oct. 17, 2010.
Product brochure for Aquabeautine XL®, by Aqua Bio Technology AS, Oslo, Norway, dated Dec. 2011.
First sale of Aquabeautine XL® by Aqua Bio Technology AS, Oslo, Norway, occurred after May 3, 2011.
The Ageing Effects of UV Rays (http://www.everdayhealth.com/skin-and-beauty/aging-skin/effects-of-uv-radiation.aspx), available at least by Oct. 12, 2009.
English translation of Office Action dated Oct. 30, 2018, in corresponding South Korean Application No. 10-2014-7002058.

*Primary Examiner* — Kevin S Orwig
(74) *Attorney, Agent, or Firm* — Wenderoth, Lind & Ponack, L.L.P.

(57) ABSTRACT

The present invention relates to cosmetic compositions comprising polypeptides obtained or obtainable from Salmonidae hatching fluid, methods of producing said compositions and their use in various cosmetic applications to the skin, particularly for improving the cosmetic appearance of skin of a mammalian animal.

20 Claims, 8 Drawing Sheets
Specification includes a Sequence Listing.

SEQUENCE LISTING

<160> NUMBER OF SEQ ID NOS: 4

<210> SEQ ID NO 1
<211> LENGTH: 255
<212> TYPE: PRT
<213> ORGANISM: Salmo salar

<400> SEQUENCE: 1

Met Arg Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

```
Gln Ile Asp Ala Gly Leu Gly Gln Val Val Ala Thr Asp Thr Ser Gln
             35                  40                  45

Ile Pro Tyr Tyr Leu Val Gly Asp Lys Trp Ile Arg Leu Pro Gly Ser
 50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                 85                  90                  95

Gly Leu Leu Lys Gln Leu Asp Ala Gly Gly Glu Gln Phe Ile Val Gly
            100                 105                 110

Ala Asn Met Asn Asp Thr Pro Tyr Cys Leu Thr Ser Ser Ala Thr Val
            115                 120                 125

Gly Tyr Lys Gly Pro Gly Ser Pro Leu Pro Trp Thr Gly Leu Pro Gly
        130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Ala Val Thr Met Val Cys Thr His
                245                 250                 255

<210> SEQ ID NO 2
<211> LENGTH: 208
<212> TYPE: PRT
<213> ORGANISM: Salmo salar

<400> SEQUENCE: 2

Ser Ile Pro Tyr Tyr Leu Val Gly Asp Lys Trp Ile Arg Leu Pro Gly
1               5                  10                  15

Ser Leu Lys His Ile Thr Val Gly Pro Ala Gly Ile Trp Gly Val Asn
            20                  25                  30

Lys Asp Tyr Ala Ile Tyr Lys Tyr Val Ala Gly Asn Trp Val Gln Ala
        35                  40                  45

Ala Gly Leu Pro Lys Gln Leu Asp Ala Gly Gly Glu Gln Phe Ile Val
    50                  55                  60

Gly Ala Asn Met Asp Asp Thr Pro Tyr Cys Leu Thr Ser Ser Ala Thr
65                  70                  75                  80

Val Gly Tyr Lys Gly Pro Gly Ser Pro Leu Pro Trp Thr Gly Leu Pro
                85                  90                  95

Gly Ala Val Lys Tyr Tyr Ser Cys Gly Pro Phe Gly Cys Trp Ala Val
            100                 105                 110

Asn Lys Asn Asp Asp Ile Tyr Leu Met Ser Leu Asn Gln Asp Cys Gln
        115                 120                 125

Asn Asn Gly Trp Ser His Ile Glu Gly Lys Leu Ser Met Ile Glu Val
    130                 135                 140

Ala Thr Asp Gly Ser Val Phe Gly Val Asn Ser Ala Gly Ser Val Tyr
145                 150                 155                 160
```

```
Thr Arg Asp Gly Ile Thr Ala Ser Lys Pro Glu Gly Thr Gly Trp Ser
            165                 170                 175

Asn Ile Pro Met Cys Met Leu Met Gly His Val Thr Tyr Asp Leu Gly
        180                 185                 190

Arg Leu Trp Val Val Ser Lys Ser Ala Val Thr Met Val Cys Thr His
        195                 200                 205

<210> SEQ ID NO 3
<211> LENGTH: 255
<212> TYPE: PRT
<213> ORGANISM: Salmo salar

<400> SEQUENCE: 3

Met Arg Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Ser Gln
        35                  40                  45

Ile Pro Tyr Tyr Leu Val Gly Asp Lys Trp Ile Arg Leu Pro Gly Ser
    50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Asn Gln Phe Val Val Gly
            100                 105                 110

Ala Asn Met Asp Asp Thr Pro Phe Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly His Phe Gly Cys Trp Ala Val Asn
145                 150                 155                 160

Lys Asn Asp Asp Ile Phe Leu Met Ser Leu Asn Gln Asp Cys Gln Asn
                165                 170                 175

Asn Gly Trp Ser His Ile Asp Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Gly Gly Thr Met Val Cys Thr His
                245                 250                 255

<210> SEQ ID NO 4
<211> LENGTH: 255
<212> TYPE: PRT
<213> ORGANISM: Salmo salar

<400> SEQUENCE: 4

Met Gly Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30
```

-continued

```
Gln Ile Asp Ala Gly Leu Gly Gln Val Val Ala Thr Asp Thr Ser Gln
    35                  40                  45

Ile Pro Tyr Tyr Leu Val Gly Asp Lys Trp Ile Arg Leu Pro Gly Ser
50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Glu Gln Phe Ile Val Gly
            100                 105                 110

Ala Asn Met Asn Asp Thr Pro Tyr Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Tyr Lys Ser Ala Val Thr Met Val Cys Thr His
                245                 250                 255
```

METHODS FOR THE PRODUCTION OF A COSMETIC COMPOSITION COMPRISING LEUKOLECTIN AND USES THEREOF

The present invention relates to the use of a polypeptide, which is derivable from Salmonidae hatching fluid, in various applications to the skin. In particular, the polypeptide as defined herein, and compositions comprising said polypeptide, is/are useful for altering, preferably improving, the cosmetic appearance of skin.

The skin is one of the more vulnerable organs of the body. Skin is in constant interaction with external stimuli, directly or indirectly, and is frequently exposed to, and affected by, environmental agents. In fact, the skin can be seen as the first point of contact with the outside world. This constant exposure can result in unpleasant and/or unwanted physical and visible changes to the skin, particularly to the cosmetic appearance of skin. Whilst such changes may not threaten the health of an individual, such changes may be physically uncomfortable or visibly disagreeable. Indeed, because the skin is so visible, changes to the appearance of skin can lead to psychological stress. There is therefore a continuing need and demand for effective treatments to maintain, restore or improve the condition of the skin, and in particular to restore the youthful appearance of skin.

Skin forms the largest organ of the body, accounting for about 12-16 percent of a person's weight. It performs many vital roles as both a barrier and a regulating influence between the outside world and the controlled environment within our bodies.

Skin consists of 3 layers, namely the epidermis, dermis and subcutis. The epidermis is the uppermost, epithelial layer of the skin. It acts as a physical barrier, preventing loss of water from the body, and preventing entry of substances and organisms into the body. Its thickness varies according to body site.

The epidermis consists of stratified squamous epithelium, i.e. it consists of layers of flattened cells. Skin, hair and nails are keratinised, meaning they have a dead, hardened hydrophobic surface made of a protein called keratin. Epidermis is made impermeable due to its contents of extracellular lipids associated with keratinocytes, especially in the middle layer of the epidermis (stratum lucidum). Mucous membranes (e.g. of the oesophagus, oral pharyngeal cavity, reproductive organs, and others) are mainly non-keratinised and moist. The epidermis has three main types of cell, namely keratinocytes (skin cells), melanocytes (pigment-producing cells) and Langerhans cells (immune cells). The Merkel cell is a fourth, less prevalent, epidermal cell.

The keratinocytes mature and differentiate with accumulation of keratin as they move outwards. They eventually fall or rub off. They form four or five distinct strata, which from the most superficial to the deepest are (i) the Stratum corneum (horny layer) with dead, dried-out hard cells without nuclei, (ii) the Stratum *granulosum* (granular layer) with cells containing basophilic granules and outwardly separated from stratum corneum by the thin stratum lucidum, (iii) the Stratum *spinulosum* (spinous, spiny or prickle cell layer) in which the cells become increasingly flattened as they move upward and (iv) the Stratum basale (basal layer) with columnar (tall) regenerative cells.

Immediately below the epidermis is the basement membrane, a specialised structure that lies between the epidermis and dermis.

The dermis is the fibrous connective tissue or supportive layer of the skin. The major fibres are collagen fibres and elastin which are interwoven.

The subcutis is the fat layer immediately below the dermis and epidermis. It is also called subcutaneous tissue, hypodermis or panniculus. The subcutis mainly consists of fat cells (adipocytes), nerves and blood vessels.

New epithelial skin cells are created in the skin's lower layer, the stratum *granulosum*. Over time, cells migrate to the surface of the skin and become more acidic. During their 30 day journey, they die and become saturated with keratin. Keratin and associated lipids are important because they protect the skin from outside elements.

Many factors may contribute to the deterioration in the cosmetic appearance of skin including disease, injury, environmental factors, age, hormone levels, medication, externally applied or ingested materials, genetic conditions or a combination of these and other factors. Age related deterioration in the cosmetic appearance of skin is a universal factor, particularly photoageing, i.e. Dermatoheliosis. This deterioration can be seen in irregularities or abnormalities in the skin, which may appear as, e.g. dry skin, wrinkles, fine lines, increased laxity (sagging) or altered pigmentation.

Photoageing is a term used for the characteristic changes induced by chronic UVA and UVB exposure. The deterioration of biological functions and ability to manage metabolic stress is one of the major consequences of the ageing process. Ageing is a complex, progressive process which also leads to functional and aesthetic changes in the skin.

Photoageing is a process of ageing of the skin attributed to continuous, long-term exposure of skin to ultraviolet (UV) radiation of approximately 245-290 nm, which may be from natural or synthetic light. Photoageing is thus also known as ageing of the skin, particularly of the face, ears, neck and hands, caused by UVA and UVB rays.

Dry and/or scaling skin is one of the most common signs of ageing skin. Although certain individuals are more susceptible to dry and/or scaling skin, the appearance of dry and/or scaling skin can affect anyone, regardless of age, gender, or skin type.

Dry skin occurs when the skin's outer layer (the stratum corneum with the stratum lucidum) is depleted of water, i.e. via trans-epidermal water loss (TEWL). When this layer is well-moistened, it minimizes water loss through the skin and helps keep out irritants, allergens, and germs. However, when the stratum corneum dries out, its protective function is reduced. This allows greater water loss, leaving skin vulnerable to environmental factors.

Ideally the stratum corneum has a water content of 10% to 30%. This water imparts to the skin its soft, smooth, and flexible texture, i.e. the characteristics associated with the youthful appearance of skin. The water comes from the atmosphere, the underlying layers of skin, and sweat. Oil produced by skin glands and fatty substances produced by skin cells act as natural moisturizers, allowing the stratum corneum to seal in water.

The body continuously loses water from the skin's surface by evaporation (TEWL). Under normal conditions, the rate of loss is slow, and the water is adequately replaced. Characteristic signs and symptoms of dry skin occur when the water loss exceeds the water replacement, and the stratum corneum's water content falls below 10%.

Moisturizers which improve or eradicate dry and/or scaling skin, thereby improving the cosmetic appearance of skin, are highly desirable. Whilst many moisturizers are known in the art, there remains a need for natural products which are effective yet gentle.

Epidermal cells exhibiting a undesired or excessive pigmentation, i.e. hyper-pigmentation, e.g. liver spots, is another common sign of ageing skin. Traditionally exfoliation may be used to remove epidermal cells that are detrimental to the cosmetic appearance of skin.

Exfoliation removes the outer strata of epidermis to reveal the newer skin cells beneath. Exfoliation may be achieved by physical means (i.e. abrasion of the skin) or by chemical means. Chemical exfoliants include scrubs containing salicylic acid, glycolic acid, fruit enzymes, citric acid or malic acid and may be applied in high concentrations by a dermatologist, or in lower concentrations in over-the-counter products. Chemical exfoliation may involve the use of products that contain alpha hydroxy acids (AHAs) or beta hydroxy acids (BHAs), or enzymes that act to loosen the glue-like substances that hold the cells together at cell junctions, allowing them to ease away. This type of exfoliation is recommended for people treating acne.

The greatest disadvantage to exfoliation is the high price of some of the products and methods used to achieve it. Exfoliation will lead to some initial redness to the skin. Near the end of chemical peels, the skin will frost, with colours varying from a bright white to gray on the skin surface.

Hence, effective methods to reduce hyperpigmentation of skin, which are gentler on the skin than exfoliation, are therefore desirable.

In addition to ageing, physical damage may reduce the cosmetic/aesthetic appearance of skin. For instance, superficial damage to the upper (surface) layers of the skin, i.e. epidermis and/or dermis by, e.g. minor scrapes, scratches etc. may result in undesirable blemishes on the skin. Physical damage to the skin, such as caused by wounds, cuts, infection, acne etc. may result in scarring.

Wounds are external or internal injuries caused by inter alia, mechanical, chemical, thermal or pathogenic means which result in the physical disruption of structural tissue integrity.

Scars are areas of fibrous tissue (fibrosis) that replace normal skin after injury. A scar results from the biological process of wound repair in the skin and other tissues of the body. Thus, scarring is a natural part of the healing process. With the exception of very minor lesions, every wound (e.g. after accident, disease, or surgery) results in some degree of scarring.

Scar tissue is both functionally and cosmetically inferior to normal uninjured skin. This inferiority is believed to be a consequence of the arrangement of collagen bundles within the dermis generated during new tissue formation. The collagen bundles within normal skin are arranged in a complex 3-dimensional woven arrangement (often termed a "basket-weave" arrangement), which provides high levels of elasticity, and resilience to damage, to the skin. Collagen bundles within scar tissue are arranged in a more planar manner, with bundles orientated parallel to the surface of the skin. The loss of 3-dimensional weave and its replacement with a parallel array of collagen bundles is believed to be responsible for the loss of cosmesis at sites of tissue scarring.

Scarring may result also from disruption of individual layers of the skin. For instance, stretch marks (also known as striae) are caused by tearing of the dermis. Stretch marks are often the result of the rapid stretching of the skin associated with rapid growth (common in puberty) or weight gain (e.g. pregnancy, muscle building, or rapid gain of fat) or, in some cases, severe pulling force on skin that overcomes the dermis's elasticity. Stretch marks may also be influenced by hormonal changes associated with puberty, pregnancy, muscle building, hormone replacement therapy for transsexuals, etc. These kinds of markings are known as striae atrophicae, striae vergetures, striae distensae, striae cutis distensae, striae gravidarum (in cases where it is caused by pregnancy), lineae atrophicae, linea albicante, or simply striae.

There thus remains a need for treatments suitable for promoting the aesthetic appearance of skin. In other words, methods of improving the cosmetic appearance of skin are desirable. In particular, there is a demand for methods for restoring the youthful appearance to aged skin and/or combating the signs of ageing skin. There is also a need for methods for improving, restoring or combating the appearance of superficially damaged skin, e.g. scarred skin or blemishes resulting from minor damage to the epidermis and/or dermis.

Certain molecules which are found in Salmonidae hatching fluid, namely a polypeptide which is known as leukolectin, have surprisingly now been found to be remarkably effective at improving the cosmetic appearance of skin, particularly reducing the physical signs associated with ageing skin and restoring the appearance of superficially damaged skin.

Initially the protein was identified in and purified from fish and described in WO 2010/049688, which is hereby incorporated by reference in its entirety. The salmon protein has 255 amino acids (SEQ ID NO: 1). This is the propeptide form of the polypeptide, which contains a 19 amino acid N-terminal peptide which suggests that it is targeted to the lysosome for later secretion (i.e. into the perivitelline space).

The amino acid sequence of the polypeptide allowed the development of epitope-specific antibodies, which in turn enabled the identification of many (2-8) seeming isoforms of the protein, depending on the tissue analyzed. At least two mRNAs have been isolated from salmon, which contain minor sequence differences that result in only 7 changes at the polypeptide level. Truncated forms of the protein have also been identified from salmon leukocytes (see SEQ ID NO: 2).

The protein bears little resemblance to any known proteins, showing overall similarity of less than 50% to any known protein. Some similarity was observed in small domains to tachylolectins.

These proteins have surprisingly been found to have pronounced effects on the cosmetic appearance of skin. Whilst not wishing to be bound by theory, the Examples demonstrate that leukolectin is capable of inhibiting the release of matrix metalloproteinases (MMPs), which are zinc dependent endopeptidases, from dermal fibroblasts. These enzymes are capable of degrading many different types of proteins present in the extracellular matrix of the skin, e.g. collagen, and it is believed that the inhibition of the release of these enzymes is, at least in part, responsible for the effects of these proteins on the cosmetic/aesthetic appearance of the skin.

Accordingly, at its broadest, the invention can be seen to provide polypeptides as described herein for use in, or in methods for, promoting the aesthetic appearance of skin. In other words, polypeptides as described herein for use in, or in methods for, improving the cosmetic appearance of skin. In a particularly preferred aspect, the invention may be seen as providing polypeptides as described herein for use in, or in methods for, restoring the youthful appearance to aged skin and/or combating the signs of ageing skin. Another preferred aspect of the invention may be seen as the provision of polypeptides as described herein for use in, or in methods for, improving, restoring or combating the appearance of superficially damaged skin, e.g. scarred skin or blemishes resulting from minor damage to the epidermis and/or dermis.

It will be evident from the disclosures below that the polypeptides as described herein may be provided in cosmetic compositions, which comprise one or more physiologically or pharmaceutically acceptable excipients and/or diluents.

Thus, in one aspect the present invention provides:

(i) a polypeptide comprising an amino acid sequence as set forth in any one of SEQ ID Nos. 1-4 or a sequence which is at least 90% identical to said sequence, or a portion of any of said sequences; or (ii) a cosmetic composition comprising (i) and one or more physiologically or pharmaceutically acceptable excipients and/or diluents, for use in improving the cosmetic appearance of the skin of a mammalian animal.

The invention also provides a method for improving the cosmetic appearance of the skin of a mammalian animal wherein a polypeptide or cosmetic composition as defined above is administered to said animal.

A further aspect of the invention is the use of a polypeptide or cosmetic composition as defined above in the manufacture of a medicament for improving the cosmetic appearance of the skin of a mammalian animal.

"Polypeptides" as referred to herein are molecules with preferably more than 50, 100, 150, 200 or 250 residues and/or less than 500, 400, 300, 200 or 100 residues or a range selected therefrom. As referred to herein a "portion" preferably comprises at least 30, 40, 50, 60, 70, 80, 90, 100, 110, 120, 130, 140, 150, 160, 170, 180, 190, 200, 210, 220, 230, 240 or more amino acids of the sequence from which it is derived. Said portion may be obtained from a central or N-terminal or C-terminal portions of the sequence. Preferably said portion is obtained from the N-terminal end, e.g. from the first 50, 100 or 150 residues of the polypeptide. Alternatively preferred are portions obtained from the C-terminal end, e.g. from the last 50, 100 or 150 residues of the polypeptide. Particularly preferred aspects include truncations of said polypeptides, e.g. to remove a signal peptide or portion absent in naturally occurring variants. Preferred truncations occur at the N-terminal end and are from 1 to 50, e.g. 1 to 10, 20, 30 or 40, or 5 to 40, e.g. 10 to 35 residues in length.

Preferably said sequence is at least 95, 96, 97, 98 or 99% identical to the sequence to which it is compared.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids.

Preferably said comparison is made over the full length of the sequence, but may be made over a smaller window of comparison, e.g. less than 200, 100 or 50 contiguous amino acids.

Preferably such sequence identity related polypeptides are functionally equivalent to the polypeptides which are set forth in the recited Sequence Nos. Such functionally equivalent polypeptides may take the form of derivatives as set forth below.

Similarly, the polypeptides with sequences as set forth in the Sequence Nos. may be modified without affecting the sequence of the polypeptide as described below.

Furthermore, "portions" as described herein may be functional equivalents. Preferably these portions satisfy the identity (relative to a comparable region) conditions mentioned herein.

As referred to herein, to achieve "functional equivalence" the polypeptide may show some reduced efficacy in performing the cosmetic function relative to the parent molecule (i.e. the molecule from which it was derived, e.g. by amino acid substitution), but preferably is as efficient or is more efficient. Thus, functional equivalence relates to a polypeptide which is effective to improve the cosmetic appearance of skin as described hereinafter. This may be tested by comparison of the effects of the derivative polypeptide relative to the polypeptide from which it is derived in a qualitative or quantitative manner, e.g. by performing the in vivo analyses referred to in the Examples. Where quantitative results are possible, the derivative is at least 30, 50, 70 or 90% as effective as the parent polypeptide. Alternatively, in vitro testing may be performed, e.g. by analysis the inhibition of the release of MMPs in in vitro cell cultures.

Functionally-equivalent proteins which are related to or derived from the naturally-occurring protein, may be obtained by modifying the native amino acid sequence by single or multiple amino acid substitution, addition and/or deletion (providing they satisfy the above-mentioned sequence identity requirements), but without destroying the molecule's function. Preferably the native sequence has less than 20 substitutions, additions or deletions, e.g. less than 10, 5, 4, 3, 2, or 1 such modifications. Such proteins are encoded by "functionally-equivalent nucleic acid molecules" which are generated by appropriate substitution, addition and/or deletion of one or more bases.

Preferred functional equivalents are "addition" variants in which amino and/or carboxy terminal fusion proteins or polypeptides are generated, comprising an additional protein or polypeptide fused to the parent polypeptide.

Particularly preferred functionally-equivalent variants are natural biological variations, particularly allelic variants or geographical variations within a species or alternatively in different genera from the family Salmonidae, especially the sub-families Salmo and Oncorhynchus and derivatives prepared using known techniques. Particularly preferred species of the Salmonidae family include Atlantic Salmon (*Salmo salar*) and Pacific Salmon (*Oncorhynchus masou*).

The polypeptides as described above, include those which are modified without affecting the sequence of the polypeptide, e.g. by chemical modification, including by deglycosylation or glycosylation. Such polypeptides may be prepared by post-isolation modification of the polypeptide without affecting functionality, e.g. certain glycosylation, methylation etc. of particular residues.

The polypeptides for use according to or in compositions of the invention may also take the form of peptidomimetics which may be considered derivatives in which the functional features of the polypeptide are retained but are presented in the context of a different, e.g. non-peptide structure. Such peptidomimetics have successfully been developed and used for other, particularly medical, applications.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudo-peptides and cyclic peptides. Structural elements considered redundant for the function of the peptide may be minimized to retain a scaffold function only or removed where appropriate.

When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the polypeptides of the invention are retained. The peptidomimetics are referred to as being "derivable from" a certain polypeptide sequence. By this it is meant that the peptidomimetic is designed with reference to a defined polypeptide sequence, such that it retains the structural features of the peptide which are essential for its function. This may be the particular side chains of the polypeptide, or hydrogen bonding potential of the structure. Such features may be provided by non-peptide components or one or more of the amino acid residues or the bonds linking said amino acid residues of the polypeptide may be modified so as to improve certain functions of the polypeptide such as stability or protease resistance, while retaining the structural features of the polypeptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |

TABLE 1-continued

| Non-conventional amino acid | Code | Non-conventional amino acid | Code |
|---|---|---|---|
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

Non-standard amino acids which may be used include conformationally restricted analogs, e.g. such as Tic (to replace F), Aib (to replace A) or pipecolic acid (to replace Pro).

The polypeptides discussed above also include derivatives which have been modified, e.g. to facilitate their use in cosmetic applications (discussed herein), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned polypeptides or nucleic acid molecules.

The polypeptides also encompass derivatives in the form of "pro-drugs" or "pro-peptides" such that the added component may be removed by cleavage once administered, e.g. by cleavage of a substituent added through esterification which may be removed by the action of esterases. Such pro-drugs include native precursors of the naturally occurring proteins which are cleaved e.g. by proteolysis to yield the polypeptide of interest. Such precursors may be inactive in the precursor form but may be activated by proteolytic cleavage. Modified polypeptides as described above may be tested to ensure that they retain functional activity relative to the unmodified molecule by determining if they have the same or similar medical effects.

The polypeptides used in compositions and uses of the invention as described herein are obtained or derived from naturally occurring sources.

Conveniently the polypeptides are isolated in accordance with the protocols described in the Examples. Such methods and the products of such methods form further aspects of the invention.

Thus in a further aspect the present invention provides a method of (i) isolating a polypeptide or (ii) preparing a cosmetic composition as described herein from Salmonidae hatching fluid (e.g. salmon hatching fluid) comprising at least the steps of:

a) suspending Salmonidae eggs in a minimal volume of water (e.g. equivalent to the volume of the eggs or less);

b) inducing synchronized, rapid hatching of said eggs (preferably such that hatching is complete within less than 2 hours for more than 95% of the embryos);

c) optionally filtering the hatched eggs to obtain hatching fluid; and d) filtering the hatching fluid to obtain the polypeptide and/or composition.

Optionally, the product obtained or obtainable from the above method may be diluted or concentrated to an appropriate concentration prior to its use in the methods and uses of the invention.

In a first embodiment, the step of filtering the hatching fluid may comprise a number of steps including:

(i) filtering the hatching fluid using a filter with a pore size of at least 5 μm, preferably 5-15 μm, and particularly preferably a pore size of 7 μm, and collecting the filtrate;

(ii) filtering the filtrate from step (i) using a filter with a pore size of 0.30-0.60 μm, preferably a pore size of 0.35-0.55, particularly preferably 0.40-0.50 μm, most preferably 0.45 μm, and collecting the filtrate;

(iii) exchanging the water in the filtrate from step (ii) with a pharmaceutically acceptable buffer;

(iv) filtering the solution obtained from step (iii) using a filter with an exclusion size of at least 80 kDa, preferably 80-120 kDa, most preferably an exclusion size of 100 kDa, and collecting the filtrate; and (v) filtering the filtrate from step (iv) using a filter with a pore size of 0.15-0.30 μm, preferably a pore size of 0.22 μm and collecting the filtrate, wherein said filtrate provides a composition comprising said polypeptide. The product obtained by this method forms a further aspect of the invention.

Alternatively, in a second embodiment, the step of filtering the hatching fluid may comprise a number of steps including:

(i) filtering the hatching fluid using a filter with a pore size of at least 5 µm, preferably 5-15 µm, and particularly preferably a pore size of 7 µm, and collecting the filtrate;

(ii) subjecting the filtrate from step (i) to ion exchange chromatography and collecting the eluate;

(iii) exchanging the water in the eluate from step (ii) with a pharmaceutically acceptable buffer; and (iv) filtering the solution obtained from step (iii) using a filter with a pore size of 0.15-0.30 µm, preferably a pore size of 0.22 µm and collecting the filtrate, wherein said filtrate provides a composition comprising said polypeptide or portion thereof. The product obtained by this method forms a further aspect of the invention.

In some embodiments it may be beneficial to subject the filtrate from step (i) to a further filtration step using a filter with a pore size that is smaller than the first filtration step. This may help to prevent material from the hatching fluid from clogging the ion exchange column (i.e. inhibiting the flow of liquid through the ion exchange column). Thus, the step of filtering the hatching fluid may comprise an optional step of:

(i') filtering the filtrate from step (i) using a filter with a pore size of 0.30-0.60 µm, preferably a pore size of 0.35-0.55, particularly preferably 0.40-0.50 µm, most preferably 0.45 µm, and collecting the filtrate.

Preferably the optional filtration step occurs before the step of subjecting the filtrate from (i) to ion exchange chromatography. Thus, the filtrate subjected to ion exchange chromatography may be from step (i) or step (i').

In an exemplary embodiment step (ii) comprises:

(a) loading the filtrate (from step (i) or step (i')) on to an ion exchange column, such as a DEAE (diethylaminoethyl) column;

(b) washing the column with a suitable buffer, e.g. a wash solution comprising 20 mM Tris-HCl, pH 8.5;

(c) eluting the polypeptide from the column using a elution buffer or solvent, such as the wash solution further comprising a salt, e.g. 50 mM NaCl; and (d) collecting the eluate from step (c).

Thus a general method of filtering hatching fluid may comprise steps (i) from the above methods; step (ii) from the above first method using a filter with a pore size of 0.30-0.60 µm and/or step (ii) from the above second method using ion exchange chromatography; step (iii) from the above methods; optionally step (iv) from the above first method using a filter with an exclusion size of at least 80 kDa and step (v) of the above first method (the equivalent of step (iv) of the above second method) using a filter with a pore size of 0.15-0.30 µm.

Whilst the filtrate may itself form the cosmetic composition, optionally the product (the filtrate of step (v) of the first embodiment or step (iv) of the second embodiment) obtained or obtainable from the above methods may be diluted (or concentrated) to an appropriate concentration prior to its use in the methods and uses of the invention. Thus, the methods may comprise a further step of diluting (or concentrating) the composition. Preferably the filtrate may be diluted (or concentrated) by a factor of at least 1.5, 2, 3, 4, 5, 10, 15, 20, 50, 100, 1000, 5000 or 10000.

Optionally, one or more pharmaceutically acceptable excipients and/or diluents may be added to the product obtained or obtainable from the above methods. Thus, the methods may comprise a further step of adding one or more pharmaceutically acceptable excipients and/or diluents to the composition or combining the composition with one or more pharmaceutically acceptable excipients and/or diluents. Alternative or additional preparation method steps include changing or modifying the solvent, e.g. pH, ion concentration etc.

Other pharmaceutically acceptable components or ingredients may be added to the product obtained or obtainable from the above methods. The one or more other components may be active components, i.e. components that have an effect on the skin, preferably that also act to promote the aesthetic appearance of skin or improve the cosmetic appearance of skin, e.g. in the cosmetic indications described herein. Thus, alternatively or additionally, the methods may comprise a further step of adding one or more pharmaceutically acceptable active components to the composition or combining the composition with one or more pharmaceutically acceptable active components. Pharmaceutically acceptable active components may include minerals, vitamins, enzymes, proteins, peptides, amino acids, lipids, antioxidants, polysaccharides, substances suitable as sunscreen filters, chemical exfoliants, extracts and mixtures thereof, as described in more detail below.

The isolated polypeptide and/or cosmetic composition obtained or obtainable from the above methods is suitable for use in the methods of the invention, as described elsewhere herein. In particularly, the cosmetic composition is for use in improving the cosmetic appearance of skin in a mammalian animal.

The step of subjecting the filtrate to ion exchange chromatography may be performed using any suitable method that results in a filtrate in which the polypeptides of the invention (including portions thereof as defined above) are enriched relative to at least one of the other polypeptides present in the hatching fluid extract prior to purification (i.e. prior to ion exchange chromatography). For instance, ion exchange chromatography may result in an eluate in which the polypeptides of the invention are enriched by at least 5% relative to at least one of the other polypeptides, preferably all of the other polypeptides, present in the hatching fluid extract prior to this step of purification. Other polypeptides may be defined as polypeptides that do not fall within the structural and/or functional definition of a polypeptide for use in the methods of the invention (i.e. a leukolectin) as defined above. Preferably, the polypeptides are enriched by at least 10, 20, 30, 40 or 50% by this step. Especially preferably the polypeptide is purified to a degree of purity of more than 50 or 60%, e.g. >70, 80 or 90%, preferably more than 95 or 99% purity relative to at least one of the other polypeptides present in the hatching fluid extract prior to purification. Thus, the eluate may comprise only trace amounts of other polypeptides that are present in the hatching fluid prior to ion exchange chromatography, e.g. less than 0.1%, 0.01%, 0.001%, 0.0001% or 0.00001% w/w.

Ion exchange chromatography is well known in the art and suitable ion exchange columns are commercially available. In an exemplary embodiment the ion exchange column is a DEAE (diethylaminoethyl) column, i.e. a column of an inert matrix, such as cellulose, silica, sepharose etc. which has been coupled to DEAE. However, other ion exchange columns may be suitable for use in the method described above.

The step of loading the filtered hatching fluid on to the ion exchange column comprises applying the hatching fluid to an ion exchange column that has been prepared or activated such that it is capable of binding the polypeptides of the invention. Preparing or activating the ion exchange column typically involves washing the column with a buffer, e.g. the wash buffer as defined below. This pre-wash step results in an ion exchange column which is under optimum conditions, e.g. pH, to enable the polypeptides to bind to the column. Thus, the loading step may be viewed as a step of binding the polypeptides of the invention to an ion exchange column.

Following the step of loading the filtered hatching fluid on to the ion exchange column, and in accordance with standard protocols, the column may be washed with a suitable buffer to remove unwanted components present in the hatching fluid that are not bound to the column. Washing comprises applying a volume of wash buffer to the column, typically the volume of wash buffer applied to the column is at least equal to the volume of the ion exchange column and may be more, e.g. at least 1.5, 2, 3, 4 or 5 times the volume of the column. In some embodiments the wash step may be repeated, e.g. 2, 3, 4, 5 or more times. Any suitable wash buffer may be utilised in the method of the invention. A suitable wash buffer is one that does not disrupt significantly the interaction between the polypeptides of interest and the ion exchange column, e.g. less than 10%, e.g. less than 5, 4, 3, 2 or 1%, of the polypeptides of the invention is removed from the ion exchange column by each wash step. In a preferred embodiment the wash buffer is a solution of Tris-HCl in the range of 10-100 mM, preferably 10-50 mM, e.g. 20-30 mM, with a pH in the range of 6-10, preferably 7-9, e.g. 8.5. The flowthrough from the wash step may be collected, e.g. to determine whether further wash steps are required (e.g. tested for the presence of polypeptides, polysaccharides, salts etc that represent unwanted components present in the hatching fluid prior to purification) and/or discarded.

The step of eluting the polypeptide from the ion exchange column may be performed by any suitable means and typically involves the application of a solvent or solution to the column to disrupt the interaction between the polypeptide of interest and the ion exchange column. Typically the volume of elution buffer or solvent applied to column is at least equal to the volume of the ion exchange column and may be more, e.g. at least 1.5, 2, 3, 4 or 5 times the volume of the column. In some embodiments the elution step may be repeated, e.g. 2, 3, 4, 5 or more times. The eluate (the flowthrough from the elution step) may be collected from each elution step and one or more of the eluates may be combined prior to the step of exchanging the water in the eluate. A suitable elution buffer or solvent is one which disrupts the interaction between the polypeptides of the invention and the ion exchange column, e.g. at least 70%, preferably at least 75, 80, 85, 90, 95 or 99%, of the polypeptides of the invention bound to the column is eluted from the column by each elution step.

In a preferred embodiment the elution buffer is the same as the wash buffer also comprising a substance capable of disrupting the interaction between the polypeptides and the ion exchange column, e.g. a salt. Thus, in some embodiments the elution buffer is a solution of Tris-HCl in the range of 10-100 mM, preferably 10-50 mM, e.g. 20-30 mM, with a pH in the range of 6-10, preferably 7-9, e.g. 8.5 also comprising a salt, e.g. NaCl, KCl etc. in the range of 10-500 mM, preferably 20-400 mM, 30-300 mM, 40-200 mM or 50-100 mM, e.g. 50 mM NaCl.

The step of exchanging the water in the filtrate or eluate may be performed using any suitable method known in the art, e.g. dia-filtration or dialysis. In a particularly preferred embodiment, this step is performed using dia-filtration using a filter with an exclusion size of less than 15 kDa, preferably 10 kDa or less, e.g. 9, 8, 7, 6, 5, 4, 3 kDa or less.

Diafiltration uses ultrafiltration membranes to remove e.g. salts or other unwanted or undesirable microsolutes from a solution or as a way of exchanging the solvent, e.g. buffer, of a solution. Small molecules are separated from a solution while retaining larger molecules in the retentate (the material which does not pass through the filter). Microsolutes and solvents, e.g. water, are generally easily washed through the membrane. Typically about 3 volumes of diafiltration solvent will eliminate 95% of the microsolute. Thus, the above filtrate from step (ii) of the first method or the eluate from step (ii) of the second method is initially processed by diafiltration and this results in the concentration of the retentate as a proportion of the solution (which contains the soluble impurities/unwanted fraction of the hatching fluid) passes through the membrane. The retentate is then diluted with a pharmaceutically acceptable buffer, e.g. 0.5 mM Sodium phosphate and 1 mM Sodium chloride, phosphate buffered saline etc. The diluted retentate may be subjected to repeated rounds of diafiltration, if necessary.

Synchronized hatching may be achieved by any suitable method known in the art. For instance, eggs may be synchronized using photo-manipulation, e.g. transferring eggs from the light (which inhibits hatching) in to conditions with no light. Manipulation of the temperature of the solution, by deoxygenation (Oppen-Berntsen et al. 1990, Aquaculture, 86, pp. 417-430), and stimulation using electricity can also be used to cause synchronized hatching. As noted above, a minimal volume of water may be equivalent to the volume of eggs or less, e.g. for every 1 ml of eggs a suspending liquid of ≤1, 0.75, 0.5, 0.25 ml may be used, e.g. from 0.5 to 1 ml.

Thus, the invention further extends to the use of polypeptides and/or compositions prepared by the above described methods.

When the polypeptide as described herein is obtained from leukocytes it is obtained in unmodified form. Polypeptides obtained from Salmonidae hatching fluid, e.g. salmon, are modified (by glycosylation and/or phosphorylation), but both forms are equally effective in the methods described herein.

The polypeptides described herein are preferably substantially free of any contaminating components derived from the source material or materials used in the isolation procedure or in their preparation. Especially preferably the compound is purified to a degree of purity of more than 50 or 60%, e.g. >70, 80 or 90%, preferably more than 95 or 99% purity as assessed w/w (dry weight). Such purity levels correspond to the specific molecule of interest, but includes its degradation products.

Where appropriate, enriched preparations may be used which have lower purity, e.g. contain more than 1, 2, 5 or 10% of the molecule of interest, e.g. more than 20, 30 or 40% as assessed w/w (dry weight). The method of "isolating" a polypeptide as described above refers to isolation to a purity as described above. The polypeptides described herein may be purified by, for example, chromatography (e.g. HPLC, size-exclusion, ion-exchange, affinity, hydrophobic interaction, reverse-phase) or capillary electrophoresis.

The polypeptides or compositions as described herein may be used in vitro, for example in cell or organ culture, to affect properties of said cells, e.g. to inhibit the release of MMPs so as to alter the structure and/or composition of the proteins of the extracellular matrix.

However, the polypeptides and compositions are preferred for use in vivo as discussed herein.

By "pharmaceutically acceptable" or "physiologically acceptable" is meant that the ingredient must be suitable for cosmetic applications and compositions. The ingredient also must be compatible with other ingredients in the composition as well as physiologically acceptable to the recipient.

The active ingredient for administration may be appropriately modified for use in a cosmetic composition. For example the compounds used in accordance with the invention may be stabilized against degradation by the use of derivatives as described above.

The active ingredient may also be stabilized in the compositions for example by the use of appropriate additives such as salts or non-electrolytes, acetate, SDS, EDTA, citrate or acetate buffers, mannitol, glycine, HSA or polysorbate.

The polypeptide or composition as described herein may be present in said compositions as the sole active ingredient or may be combined with other ingredients, particularly other active ingredients, e.g. to augment the cosmetic effect (as described above) or to make the composition more appealing to the consumer.

As mentioned above, the polypeptides and compositions as described herein exhibit properties that are useful in improving the cosmetic appearance of skin, particularly of aged skin, e.g. photo-aged skin, or scarred skin, e.g. as a result of damage of at least one layer of the skin, e.g. a wound, or blemishes or abrasions resulting from minor damage to the epidermis and/or dermis.

The composition comprising one or more polypeptides described herein may also comprise impurities, e.g. after the preparation of said one or more polypeptides of the invention from natural sources. In compositions comprising said one or more polypeptides as described herein, each of said polypeptide(s) may be present in the range 0.0001 to 50% w/w of the cosmetic composition prepared according to the above described method. Preferably said polypeptide(s) is present at a range of 0.01-40% w/w of the cosmetic composition prepared according to the above method or as described hereinafter, e.g. after further dilution. For instance, the polypeptide(s) may be present at a range of 0.0001 to 5%, 0.0001 to 3%, 0.0001 to 2%, 0.0001 to 1%, 0.0001 to 0.5%, 0.0001 to 0.1% w/w of the cosmetic composition.

The proportion of the polypeptide(s) or portions of polypeptide(s) present in the cosmetic compositions may be defined relative to the other solutes (e.g. salts) in the composition, i.e. excluding solvents, e.g. water. Thus, said polypeptide(s) or portions of polypeptide(s) may be present at the range of 10-100% w/w of the dry mass of the composition. In some embodiments the polypeptides or portions of polypeptides, in combination, may be present at the range of 10-90% w/w of the dry mass of the composition, e.g. 10-80%, 15-70%, 20-60%, 30-50% w/w of the dry mass of the composition. In other embodiments the polypeptides or portions of polypeptides, in combination, may be present at the range of 10-40%, 20-39%, 25-38%, 30-37% etc. w/w of the dry mass of the composition. As described herein the composition may be diluted for use according to the invention.

Whilst the invention is directed to methods for improving the cosmetic appearance of skin, this may include the treatment of a disorder, abnormality or condition, but in all cases the treatment is cosmetic in nature.

As referred to herein "cosmetic" is intended to refer to a treatment which does not cure, treat or prevent a disease or disorder, but instead serves as a skincare product or to modify or improve the appearance of the skin, e.g. the colour, texture or moisture content of the skin.

The basis of the treatments described herein is the skin anti-ageing, scar-reducing and anti-blemish/anti-abrasion effects of the polypeptides as disclosed herein. These effects have been shown in the Examples provided herein.

Thus treatments based on the anti-ageing, anti-blemish/anti-abrasion and scar-reducing properties of the polypeptides described herein are contemplated.

The invention thus provides a cosmetic method of improving the appearance of skin of a mammalian animal, wherein a polypeptide or cosmetic composition as described hereinbefore is administered to said animal.

In a particularly preferred embodiment the skin is aged, blemished or scarred skin.

"Aged skin" refers to skin that displays one or more signs or symptoms of ageing, i.e. the appearance of wrinkles, fine lines, hyperpigmentation, laxity (sagging), dry skin, scaling or transepidermal water loss (TEWL). In particular, "aged skin" is determined relative to normal optimum skin, i.e. healthy, hydrated, normally pigmented and non-aged skin. In this respect, aged skin need not be related to the age of the subject and may be aged prematurely, e.g. by chronic exposure to sunlight (photo-damage). Thus, the relative parameters for "normal optimum skin" may be determined as the average measurements of the above signs of ageing from a number of subjects of the same or similar age to the subject in question, e.g. subjects that have not received chronic exposure to sunlight. Alternatively, the relative parameters for "normal optimum skin" may be taken as the measurements from subjects that are younger than the subject in question. In other words, the polypeptides, uses and compositions as described herein may be used to restore the youthful appearance of skin, relative to the skin of the subject at an earlier age.

Thus, the invention provides a cosmetic method for the treatment of dermatoheliosis in a mammalian animal wherein a polypeptide or cosmetic composition as described hereinbefore is administered to said animal, preferably wherein said polypeptide or composition is administered topically.

Alternatively viewed, the invention provides a polypeptide or cosmetic composition as described hereinbefore for use in the treatment of dermatoheliosis in a mammalian animal, preferably wherein said polypeptide or composition is for administration to the skin of said animal. In a particular embodiment the polypeptide or composition is for topical administration.

In a particularly preferred embodiment, improving the cosmetic appearance of skin (e.g. aged or photo-damaged skin) involves a reduction or prevention in the cosmetic appearance or prevalence of wrinkles, fine lines, hyperpigmentation, laxity, dry skin, scaling and/or transepidermal water loss. One or more of these parameters may be improved. Preferably fine lines and/or wrinkles are reduced.

Reduction or prevention in the cosmetic appearance or prevalence of the signs or symptoms of e.g. aged skin or dermatoheliosis, may mean that there is a reduction in the number and/or severity of the sign or symptom. For instance, the number of fine lines and wrinkles may be reduced and/or the size, e.g. the depth, of the wrinkles or fine lines may be reduced or minimized. Furthermore, reduction or prevention may involve stopping, or reducing the rate of, the appearance of new signs or symptoms.

"Dry skin" as referred to herein refers to an epidermis that lacks moisture or sebum, often characterized by a pattern of fine lines, scaling, and an itching and/or burning feeling. Dry skin can occur as a skin condition in itself (e.g. due to age) or may be the symptom of a skin disorder or condition such as sun-damage.

In this respect, the reduction of dry skin, scaling, finelines or transepidermal water loss may be achieved by the moisturizing effects of the polypeptide and composition described above.

Thus, the invention may be seen to provide a cosmetic or non-cosmetic method of moisturizing skin of a mammalian animal, wherein a polypeptide or cosmetic composition as defined herein is administered to said animal.

Alternatively stated, the present invention provides a polypeptide or cosmetic composition as described herein for use in moisturizing skin of a mammalian animal. (The compound or composition may alternatively be used to prepare a cosmetic medicament for that purpose.)

"Moisturizing" as referred to herein covers moisturizers which prevent loss of water from the skin (e.g. TEWL) as well as moisturizers (humectants) that attract and retain water when applied to the skin and emollients (which improve defective desquamation).

As mentioned above, such moisturizing properties are advantageous for improving the cosmetic appearance of skin. In a particularly preferred embodiments, the skin is the skin of the face, ears, neck, hands or scalp.

"Wrinkles" are folds, ridges or creases in the skin. Skin wrinkles typically appear as a result of ageing processes. In this respect, the dermis comprises many of the structural elements of skin, which include collagen, which gives the skin its strength, glycosaminoglycans which give the skin its turgor, and elastin fibres which give the skin its elasticity or spring.

As the skin ages, the dermal layer gets thinner and the skin also produces less collagen. Moreover, the elastin fibres that provide elasticity wear out. These changes in the scaffolding of the skin cause the skin to wrinkle and sag. The rete-ridges of the dermal-epidermal junction flatten out, making the skin more fragile and making it easier for the skin to shear. This process also decreases the amount of nutrients available to the epidermis by decreasing the surface area in contact with the dermis, also interfering with the skin's normal repair process.

In the subcutaneous layer the fat cells get smaller with age. This leads to more noticeable wrinkles and sagging (laxity), as the fat cells cannot "fill in" the damage from the other layers.

Exposure to UVA and UVB radiation, i.e. sunlight, causes collagen to break down at a higher rate than with just chronologic ageing. Sunlight damages collagen fibres and causes the accumulation of abnormal elastin. When this sun-induced elastin accumulates, matrix metalloproteinases (MMP) are produced in large quantities.

Normally, metalloproteinases remodel sun-injured skin by manufacturing and reforming collagen. However, this process does not always work well and some of the metalloproteinases actually break down collagen. This results in the formation of disorganized collagen fibres known as solar scars. The repetition of this imperfect rebuilding/regeneration process causes wrinkles to develop and skin laxity.

However, as mentioned above, the polypeptides as described herein have been shown to inhibit the release of MMPs, thus the polypeptides and compositions of the invention are advantageous in reducing or preventing the formation of wrinkles and skin laxity.

In a further preferred aspect, the skin condition to be treated or prevented cosmetically is a pigmentation condition, disorder or abnormality.

Pigmentation disorders or abnormalities of the skin, i.e. hyperpigmentation, may occur as a result of age or may result from premature ageing due to e.g. sun damage. Altered pigmentation may result from a local excess of melanocytes or increases in melanocyte activity, or both. Pigmentation disorders include liver, sun or age spots (solar lentigo) and other blemishes such as freckles.

"Scarred skin" is skin that is functionally and cosmetically inferior to normal uninjured skin. As mentioned above, scarring is thought to result from the different arrangement of collagen bundles that form in healing skin.

Hence, one aspect of the present invention is the provision of a cosmetic method for reducing or minimizing scar tissue or improving cosmetic appearance of a scar in a mammalian animal wherein a polypeptide or cosmetic composition as described hereinbefore is administered to said animal, preferably wherein said polypeptide or composition is administered topically to scar tissue.

Alternatively viewed, the invention provides a polypeptide or cosmetic composition as described hereinbefore for use in reducing or minimizing scar tissue or improving cosmetic appearance of a scar in a mammalian animal, preferably wherein said polypeptide or composition is for administration to scar tissue of said animal. In a particular embodiment the polypeptide or composition is for topical administration. The cosmetic composition may also be used to treat superficially damaged skin.

There are various stages in skin healing (described in WO 2007/059584, which is incorporated herein by reference), e.g. wounds, which result in a scar or scar tissue. For superficial damage to the skin, i.e. minor damage to epidermis and/or dermis caused by, e.g. scratches or scrapes, the latter stages of skin healing are of primary importance.

The first stage is the "inflammatory" stage (0-6 days), which immediately follows the infliction of the wound, such as a cutaneous wound. This is referred to as hemostasis, whereby vasoconstriction and clotting, mediated by fibrin and platelets, are initiated to control bleeding. The clot further serves as a provisional matrix for incoming fibroblasts and inflammatory cells to the wound and as a reservoir of cytokines and growth factors.

Following hemostasis, inflammatory cells enter the wound and perpetuate the inflammatory process (manifested by erythema, heat, swelling and pain). The first of these are polymorphonuclear cells (PMNs) which are attracted by growth factors and cytokines such as platelet derived growth factor (PDGF) and IL-8. IL-8 is a major chemo-attractant for PMNs, and its rapid and transient expression is critical to the inflammatory process. PMNs begin to clean the wound by removing cellular debris, foreign particles and bacteria and are resident in the wound for a relatively short period (1-2 days). By about 3 days post-injury, PMNs are replaced by monocytes, which transform into macrophages that also act as wound cleaners. Fibrocytes play an important role in the inflammatory process and are specifically involved in collagen and cytokine production.

The second stage is the "Proliferation" stage (which occurs from 3 days—several weeks after skin damage). Migrating fibroblasts produce a permanent collagen-based extra-cellular matrix (ECM) and macrophages produce a variety of growth factors and cytokines, which in turn stimulate the production of growth factors. Matrix metalloproteinases and serine proteinases play an important role in the regulation of cellular migration and ECM remodelling following injury and it has been demonstrated that decreased ECM reorganization is associated with decreased fibroblast MMP production and activation.

Re-epithelialization is the next key event in the skin healing process and is initiated primarily by migrating keratinocytes. Re-epithelialization is achieved via growth factor and cytokine stimulated proliferation of keratinocytes, which migrate through the granulation tissue. These cells appear to undergo a number of phenotypic changes during migration, expressing proteins associated with the differentiating cellular phenotype. As migration proceeds, keratinocytes acquire a proteolytic phenotype producing serine proteinases and MMPs. The keratinocytes continue to migrate into the wound space until completion, when the mitotically active keratinocytes undergo further phenotypic alteration, such that differentiation and stratification of the epithelium and re-formation of the basement membrane occurs, to complete the re-epithelialization process.

Cellular ECM attachment, ECM degradation by proteinases and the overall regulation of these processes by cytokines and growth factors, are other key features of skin remodelling and healing, which co-ordinate cellular function, such as cell migration and wound contraction, via cellular integrin-ECM interactions. Such interactions regulate cytoskeleton reorganization and new integrin-ECM interactions, whilst proteinases remove existing integrin interactions, allowing rear de-adhesion and cell migration. Cellular contractility in the absence of rear de-adhesion results in dermal reorganization, as quantified experimentally by collagen lattice reorganization/contraction.

The final stage of skin healing (and thus scar formation) is "maturation" (which takes place between 4 days-weeks or months after the damage has occurred). Maturation (or remodelling) may take as little as days or weeks, particularly for superficial skin damage, but the complete process can last up to several years. During this phase contraction, decreased redness, decreased thickness, decreased induration and increased strength of the skin is observed. The skin or scar tissue contracts under the influence of myofibroblasts, collagen production in the granulation tissue decreases and blood vessels diminish. Skin healing is then completed by further re-epithelialization.

Thus, it will be evident from the above that the polypeptide or composition described herein may have an effect on reducing or minimizing scar tissue or improving the cosmetic appearance of a scar when applied during the process of skin healing, particularly at the proliferation or maturation stage. Thus, the products described above may be applied to areas of superficial skin damage or scars, wherein a scar may be viewed as partially or fully healed skin. In a preferred embodiment, the polypeptide or composition as described herein is for application at the maturation stage.

In a particularly preferred embodiment, the scar tissue is a result of acne.

In another preferred embodiment the scar tissue is a stretch mark or striae. Preferably the striae is selected from any one of striae atrophicae, striae vergetures, striae distensae, striae cutis distensae, striae gravidarum, lineae atrophicae or linea albicante.

As referred to herein "improving" the cosmetic appearance of skin is determined relative to normal optimum skin, i.e. healthy, hydrated, normally pigmented and non-aged skin. Hence, with respect to aged skin, one or more of the signs or symptoms of ageing may be measured as described in the Examples and compared to the same signs of skin that is chronologically or physiologically younger, preferably when an improvement is the reduction in one or more of the signs or symptoms of ageing.

With respect to scarred or blemished skin, reducing or minimizing scar tissue or improving the cosmetic appearance of a scar or blemish means that the area of the scar or blemish may show a reduction in the level or extent of scarring, redness, skin marking, or pigmentation (hyper- or hypo pigmentation) which might otherwise be associated with the process of skin healing, wherein these attributes are compared with normal, un-scarred skin. The tensile strength of the skin at and around the site of the healed skin or scar may also be measured, with an increase in the tensile strength indicating an improvement in the cosmetic appearance of the skin or a reduction in scar tissue.

In a preferred aspect the cosmetic uses are achieved by topical administration to the skin.

As used herein, "treating" refers to the reduction, alleviation or elimination, preferably to normal levels, of one or more of the cosmetic symptoms or effects of said cosmetic condition or disorder e.g. presence or extent of dry skin, extent or area of pigmentation or scarring etc. relative to the symptoms or effects present on a different part of the body of said individual where the skin does not suffer from said condition or disorder and not subject to said treatment or in a corresponding normal individual not subject to said treatment.

"Preventing" or "reducing" refers to absolute prevention, or reduction or alleviation of the extent or timing (e.g. delaying) of the onset of that symptom or effect. For example conditions typified by dry, abnormally pigmented, wrinkled or scarred skin may be prevented by regular application of compositions described herein before the appearance of such a condition.

Preferably said treatments are achieved using the polypeptides described herein. Cosmetic compositions comprising said polypeptides are particularly preferred.

The cosmetic methods of treatment or prevention according to the invention may advantageously be combined with administration of one or more active ingredients which are effective in treating or preventing the disorders or conditions and/or to achieve, e.g. moisturization. Thus, cosmetic compositions described herein may additionally contain one or more of such active ingredients.

According to a yet further aspect of the invention we provide products containing one or more polypeptides as herein defined and optionally one or more additional active ingredients as a combined preparation for simultaneous, separate or sequential use in human or mammalian animal therapy as described herein.

The compositions of the invention may be formulated in a conventional manner with one or more physiologically acceptable carriers, excipients and/or diluents, according to techniques well known in the art using readily available ingredients.

Thus, the active ingredient may be incorporated, optionally together with other active substances as a combined preparation, with one or more conventional carriers, diluents and/or excipients, to produce conventional galenic preparations such as powders, sachets, cachets, elixirs, suspensions (as infusion fluids), emulsions, solutions, syrups, aerosols (as a solid or in a liquid medium), ointments, sterile packaged powders, and the like. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like. Some of these components are described in more detail below.

Other active ingredients or components in the cosmetic composition may be selected from any one or more of minerals, vitamins, enzymes, proteins, peptides, amino acids, lipids, polysaccharides, substances suitable as sunscreen filters, chemical exfoliants, extracts, skin-conditioning agents, antioxidants and mixtures thereof.

Examples of proteins that may be combined with the composition of the invention include collagen and/or a derivative thereof (e.g. portions thereof as defined above), a protein or peptide which is capable of promoting cell growth, glycoprotein 1, glycoprotein 2 and laminin.

The composition of the invention may be combined with enzymes including, but not limited to, any one or more of, fruit enzymes (e.g. bromelain), superoxide dismutase, peroxidase, hyaluronidase and mucopolysaccharidase.

Peptides may be selected from, but are not limited to, any one or more of D,L-carnosine, D-carnosine, L-carnosine, anserine and Matrixyl (pentapeptide derivative).

Amino acids may be selected from, but are not limited to, any one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, and L-valine and derivatives thereof including non-naturally occurring amino acids as defined in Table 1. Particularly preferred amino acids as antioxidants may be selected from any one or more of glycine, lysine, arginine, cysteine, cystine, histidine, tyrosine and tryptophan.

The cosmetic composition may comprise one or more lipids which includes fats, oils, waxes and the like. Suitable polar oils are, for example, those from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil and the like.

Alternatively or additionally the oil may be selected from volatile oils, non-volatile oils or mixtures thereof. Non-volatile oils include oils that fulfill at least one of the following definitions: (a) the oil exhibits a vapour pressure of no more than 0.2 mm Hg at 25° C. and one atmosphere pressure; (b) the oil has a boiling point at one atmosphere of at least 300° C. Volatile oils include materials that are not "non-volatile" as defined above.

Non-volatile oils may be selected from non-volatile silicone oils, non-volatile hydrocarbon oils and mixtures thereof. Suitable non-volatile silicone oils include linear polymethylsiloxanes and, preferably, non-volatile silicone oils are high molecular weight dimethicones. Examples of commercially available linear polymethylsiloxanes include DC 200 Fluid 20 Cst, DC 200 Fluid 100 Cst, DC 200 Fluid 350 Cst from Dow Corning Corporation.

Suitable non-volatile hydrocarbon oils include branched esters of diglycerin or triglycerin or the esters or 1,2,3,4 butane triol or erythritol, di erythritol or tri erthyritol. Preferably, non-volatile hydrocarbon oils comprise erythrityl triethylhexanoate (available as Salacos E-38 from Nisshin Oilio) and Polyglyceryl-2 triisostearate (available as Cosmol 43V from Nisshin Oilio), diethyl hexyl carbonate (available as Tegosoft DEC from Degussa), dicapryl Ether (available as Cetiol OE from Cognis AG), dicapryl Carbonate (available as Cetiol CC from Cognis AG), isononyl isononanoate (available as Lanol 99 from Seppic), tridecyl Neopentanoate (supplied as Ceraphyl 55 from International Speciality Products), or a mixture thereof.

Volatile oils may be selected from volatile silicone oils, both functionalised and non-functionalised, volatile hydrocarbon oils and mixtures thereof. Volatile oil useful in the present invention may be saturated or unsaturated, have a straight or branched chain or a cyclic structure or have a combination of any one or more of said features.

Examples of volatile hydrocarbons oils include polydecanes such as isododecane and isodecane (e.g., Permethyl-99A which is available from Presperse Inc.) and the C7-C15 isoparaffins (such as the Isopar Series available from Exxon Chemicals).

The volatile silicone oil may be selected from cyclopentasiloxane, cyclohexasiloxane or a mixture thereof. Examples of commercially available volatile cyclic silicone oils include DC 244, DC 245, DC 344, and DC 345 from Dow Corning Corp.; SF-1204 and SF-1202 Silicone Fluids from Momentive Performance Materials; GE 7207 and 7158 from General Electric Co.); and, SWS-03314 from SWS Silicones Corp.

The linear volatile silicone oil may be a linear polymethylsiloxane. An example of commercially available linear polymethylsiloxanes include DC 200 Fluid, 5 Cst from Dow Corning Corp.

The cosmetic composition of the invention may further comprise one or more polysaccharides selected from, but not limited to, any one or more of anionic polysaccharides (e.g. alginic acid, pectin, xanthan gum, hyaluronic acid, chondroitin sulfate, gum arabic, gum karaya, gum tragacanth, carboxymethyl-chitin, cellulose gum, glycosaminoglycans), cationic polysaccharides (e.g. chitosan, acetylated chitosan, cationic guar gum, cationic hydroxyethylcellulose (HEC)), nonionic polysaccharides (e.g. starch, dextrins, guar gum, cellulose ethers such as hydroxyethylcellulose, methylcellulose and nitrocellulose), amphoteric polysaccharides (e.g. carboxymethylchitosan, N-hydroxy-dicarboxyethyl-chitosan, modified potato starch) and hydrophobic polysaccharides (e.g. cetyl hydroxyethylcellulose, polyquaternium24).

The cosmetic composition may further comprise a substance suitable as a sunscreen filter such as an organic sunscreen, e.g. a cinnamic derivative. The organic sunscreen active may be selected from hydrophilic organic sunscreen, hydrophobic organic sunscreen, or mixtures thereof. Suitable examples of sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997).

The organic sunscreen may be selected from alkyl $\beta,\beta$-diphenylacrylate derivatives, $\alpha$-cyano $\beta,\beta$-diphenylacrylate derivatives, anthranilate derivatives, benzophenone derivatives, camphor derivatives, dibenzoylmethane derivatives, p-aminobenzoic derivatives, salicylic derivatives, triazine derivatives, or mixtures thereof. For instance the hydrophobic organic sunscreen may be selected from 4-(1,1-dimethylethyl)-4'-methoxydibenzoylmethane; 4-isopropyldibenzoylmethane; 4-(1,1-dimethylethyl)-4'-methoxydibenzoylmethane, 2-ethylhexyl-2-cyano-3,3-diphenylacrylate, or a mixture thereof.

An example of commercially available 4-(1,1-dimethylethyl)-4'-methoxydibenzoylmethane, also known as butyl methoxydibenzoylmethane or Avobenzone, includes Parsol™ 1789 from Givaudan Roure S. A. and Eusolex™ 9020 from Merck & Co., Inc. An example of commercially available 4-isoproplydibenzoylmethane, also known as isopropyldibenzoylmethane, includes Eusolex™ 8020 from Merck & Co., Inc. Examples of commercially available 2-ethylhexyl-2-cyano-3,3-diphenylacrylate, also known as Octocrylene, include Uvinul N539 SG from BASF; and Eusolex OCR from Rona/Merck.

In some embodiments the hydrophilic organic sunscreen may be 2-phenylbenzimidaole-5-sulfonic acid. An example of commercially available 2-phenylbenzimidaole-5-sulfonic acid, also known as PBSA, includes Eusolex 232 from Rona/Merck.

Suitable examples of cinnamic derivative sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997). The cinnamic derivative may be selected from 2-ethylhexyl-p-methoxycinnamate, diethanolamine methoxycinnamate, 2-ethoxyethyl-p-methoxycinnamate, or a mixture thereof. For instance, the cinnamic derivative may be 2-ethylhexyl-p-methoxycinnamate.

The cosmetic composition may be combined with a chemical exfoliant selected from, but not limited to, any one more of alpha hydroxy acids (AHAs), beta hydroxy acids (BHAs) or poly-hydroxy acids, such as salicylic acid, glycolic acid, citric acid and malic acid.

Extracts that may be incorporated in the cosmetic composition include, but are not limited to plant extracts, which may comprise phenolic compounds such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordi-hydroguaiaretic acid, trihydroxybutyrophenone and derivatives thereof. Particular plant extracts for use in the composition of the invention include aloe vera extract, *ginseng* extract and horsetail extract.

*Ginseng* extract is obtainable by extracting with a hydrophilic solvent (in particular, water, ethanol, glycol, or any mixtures thereof) the root of *Panax ginseng*. The extract contains saponins, sterols, carbohydrates, pectin, vitamins, minerals and lipids.

Horsetail extract is obtainable by extracting with a hydrophilic solvent (e.g., water, ethanol, glycol, or any mixtures thereof) the whole herb of *Equisetum arvense*. The extract contains silicates, flavinoids, saponosides, caffeic acid and ferulic acid.

The cosmetic composition may further comprise a skin-conditioning agent. The skin-conditioning agent may be selected from humectants, exfoliants, emollients or mixtures thereof. Humectants includes polyhydric alcohols such as glycerine, propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerine or mixtures thereof.

Examples of antioxidants that may be combined with the composition of the invention include but are not limited to amino acids, vitamins, minerals, carotenoids, peptides, thiols, sulfoximine compounds, chelators, unsaturated fatty acids, phenolic compounds, plant extracts, stilbenes, uric acid, mannose, chlorogenic acid, imidazoles (e.g. urocanic acid), furfurylidenesorbitol, ubiquinone, ubiquinol, plastoquinone, phytosterols and derivatives thereof (e.g. salts, esters, ethers, sugars, nucleotides, nucleosides, peptides and/or lipid derivatives), some of which are described above.

Vitamins may be selected from, but are not limited to, any one or more of vitamin A and derivatives thereof (e.g. retinoid or retinol or their derivatives such as retinyl palmitate or retinyl proprionate), biotin, folic acid, calcium pantothenate, nicotinamide, pyridoxine HCl, pyridoxal HCl, riboflavin, thiamine HCl, thymidine, vitamin B12, vitamin B3 (e.g. niacinamide), vitamin B5 (e.g. panthenol), vitamin C and derivatives thereof (e.g. ascorbyl palmitate, Mg ascorbyl phosphate, ascorbyl acetate), tocopherols and derivatives (e.g. vitamin E acetate).

Minerals may be selected from, but are not limited to, any one or more salts of molybdenate (e.g. $(NH_4)OMo_7O_{24}$) aluminium (e.g. $AlCl_3$), calcium (e.g. $CaCl_2$), cobalt (e.g. $CoCl_2$), chromium (e.g. $CrK(SO_4)$), copper (e.g. $CuSO_4$), iron (e.g. $Fe(NO_3)_3$, $FeSO_4$), potassium (e.g. KCl), magnesium (e.g. $MgCl_2$), manganese (e.g. $MnCl_2$, $MnSO_4$), phosphate (e.g. $Na_2HPO_4$, $NaH_2PO_4$), carbonate (e.g. $NaHCO_3$), silicate (e.g. $Na_2SiO_3$), sodium (e.g. NaCl), vanadate (e.g. $NH_4VO_3$), nickel (e.g. $NiCl_2$), tin (e.g. $SnCl_2$), zinc (e.g., ZnO, $ZnSO_4$), selenium (e.g. selenomethionine, ebselen, $H_2SeO_3$, $Na_2SeO_3$), sulphate and nitrate.

Carotenoids, may be selected from, but are not limited to, any one or more of carotenes, e.g. $\alpha$-carotene, $\beta$-carotene, $\psi$-lycopene, phytoene etc. and derivatives thereof.

Thiols may be selected from, but are not limited to, any one or more of aurothioglucose, propylthiouracil, thioredoxin, lipoic acid, glutathione, cysteine, cystine, cystamine and their glycosyl, N-acetyl, methyl, ethyl, propyl, amyl, butyl and lauryl, palmitoyl, oleyl, $\gamma$-linoleyl, cholesteryl and glyceryl esters and the salts thereof, dilauryl thiodipropionate, distearyl thiodipropionate, thiodipropionic acid and derivatives thereof.

Sulfoximine compounds may be selected from, but are not limited to, any one or more of homocysteine sulfoximine, buthionine sulfones, penta-, hexa-, heptathionine sulfoximine, which may be included in the composition such that they are provided in very low dosages (e.g. pmol to µmol/kg).

Chelators may be selected from, but are not limited to, any one or more of apoferritin, desferral, lactoferrin, $\alpha$-hydroxy fatty acids, palmitic acid, phytic acid, $\alpha$-hydroxy acids (e.g.

citric acid, lactic acid, malic acid), humic acid, bile acid, bile extracts, bilirubin, biliverdin, EDTA, EGTA and derivatives thereof.

Unsaturated fatty acids may be selected from, but are not limited to, any one or more of γ-linolenic acid, linoleic acid, oleic acid and derivatives thereof.

Stilbenes and derivatives thereof include, for example, stilbene oxide and trans-stilbene oxide.

A variety of additional optional active ingredients may be incorporated into the cosmetic compositions of the present invention. Non-limiting examples of these additional ingredients include additional skin care actives such as farnesol, bisabolol, phytantriol, urea, guanidine (e.g. amino guanidine); hexaminidine compounds, salts or derivatives thereof; sugar amines; self-tanning agents (e.g. dehydroxyacetone); structuring agents; hydrophilic gelling agents; anti-acne medicaments (resorcinol, salicylic acid, and the like); skin soothing and healing agents such as allantoin and the like; and agents suitable for aesthetic purposes such as essential oils, fragrances, skin sensates, opacifiers, aromatic compounds (e.g. clove oil, menthol, camphor, *eucalyptus* oil, and eugenol).

The compositions described herein may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

The emulsifier may be selected from nonionic emulsifiers, anionic emulsifiers, cationic emulsifiers, zwitterionic emulsifiers, amphoteric emulsifiers or mixtures thereof. Emulsifiers are known in the art. See, e.g., McCutcheon's, Detergents and Emulsifiers, North American Edition (1986), published by Allured Publishing Corporation.

When the cosmetically acceptable carrier is a water-in-silicone emulsion, emulsifiers are preferably selected from polyoxyalkylene copolymers, polyglyceryl copolymers or mixtures thereof. Polyoxyalkylene copolymers, also known as silicone polyethers, are described in detail in U.S. Pat. No. 4,268,499. An example of commercially available polyoxyalkylene copolymers includes DC5225C or DC2-5185C (PEG/PPG-18/18 dimethicone available as blend with cyclopentasiloxane) from Dow Corning Corp.; and, KF6017 or KF6028 (PEG-9 dimethicone) from Shin-Etsu Inc. Examples of commercially available polyglyceryl emulsifiers include KF6100 and KF6104 from Shin-Etsu Inc.

Compositions are preferably for topical (i.e. to the skin) administration.

Topical compositions include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

In some embodiments the polypeptide and cosmetic compositions described herein may be topically administered to the skin via a product, device or material to which the polypeptide or composition has been applied, impregnated or chemically bonded. To this end, bandages, plasters (e.g. adhesive patches), gauze, surgical tape, cotton swabs or other absorbent materials, e.g. a puff, fleece, or sponge, or supportive matrices may be coated, impregnated or chemically bonded with a polypeptide or composition as described herein. For example, many compositions can be applied to the skin using dermal patches that are well described in the art, e.g. US 2008/0038300, US 2009/0043236, WO 2005/067499 and WO 2009/085302, which are incorporated herein by reference. In some embodiments, the material comprising the polypeptide or composition as described herein may be in the form of a device that can be, e.g. worn by the subject to be treated. For instance, the polypeptide or composition as described herein may be applied, impregnated or chemically bonded onto a material or supportive matrix that forms all or part of a diaper, glove, sock etc.

The cosmetic compositions can be included in a container, pack, or dispenser together with instructions for administration.

Hence, a further aspect of the invention comprises the provision of a product, material or device which is coated, impregnated or chemically bonded with a polypeptide or composition as described herein. The invention also extends to such products, materials or devices for uses as described herein. Preferably said product is a bandage, plaster (e.g. adhesive patch), gauze, surgical tape or cotton swab or said device is a diaper, glove or sock.

The concentration of active ingredient in compositions of the invention, depends upon the mode of administration, the course of treatment, the age and weight of the patient, the cosmetic indication, the body or body area to be treated and may be varied or adjusted according to choice. Generally however, concentration ranges for the compound described herein is 0.0001, 0.0005, 0.001 or 0.01 to 50%, e.g. 0.0005-40%, e.g. 0.01 to 25%, such as 0.1 or 0.5 to 5, e.g. 1-5% (w/w or v/v of the final preparation for administration, particularly for topical administration) e.g. a 1% solution of the aforementioned composition prepared according to the method of the invention.

When more than one compound is present, e.g. additional moisturizing agents as described herein, each compound may be present in the amounts described above. Said concentrations are determined by reference to the amount of the compound itself and thus appropriate allowances should be made to take into account the purity of the composition. Effective single doses for the polypeptides may lie in the range of from 0.001-100 mg/cm$^2$/day, e.g. 0.1-100 mg/cm$^2$/day, preferably 0.001-10 mg/cm$^2$/day, e.g. 0.1-10 mg/cm$^2$/day, when applied topically, depending on the mammalian animal being treated, taken as a single dose.

Preferably liquid solutions, creams or suspensions would be employed for topical administration of the polypeptides or compositions described herein.

Animals to which the compositions may be applied or administered are limited to mammals. Preferably the mammals are primates, domestic animals, livestock and laboratory animals. Thus preferred mammalian animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows:

FIG. 1 shows a photograph of a subject treated with the composition comprising the polypeptide of the invention before treatment (Baseline), after 2 weeks and after 12 weeks of treatment. The reduction in various signs of aged skin are evident after both 2 and 12 weeks. The values provided indicate the average changes for 35 participants.

Figure 1:
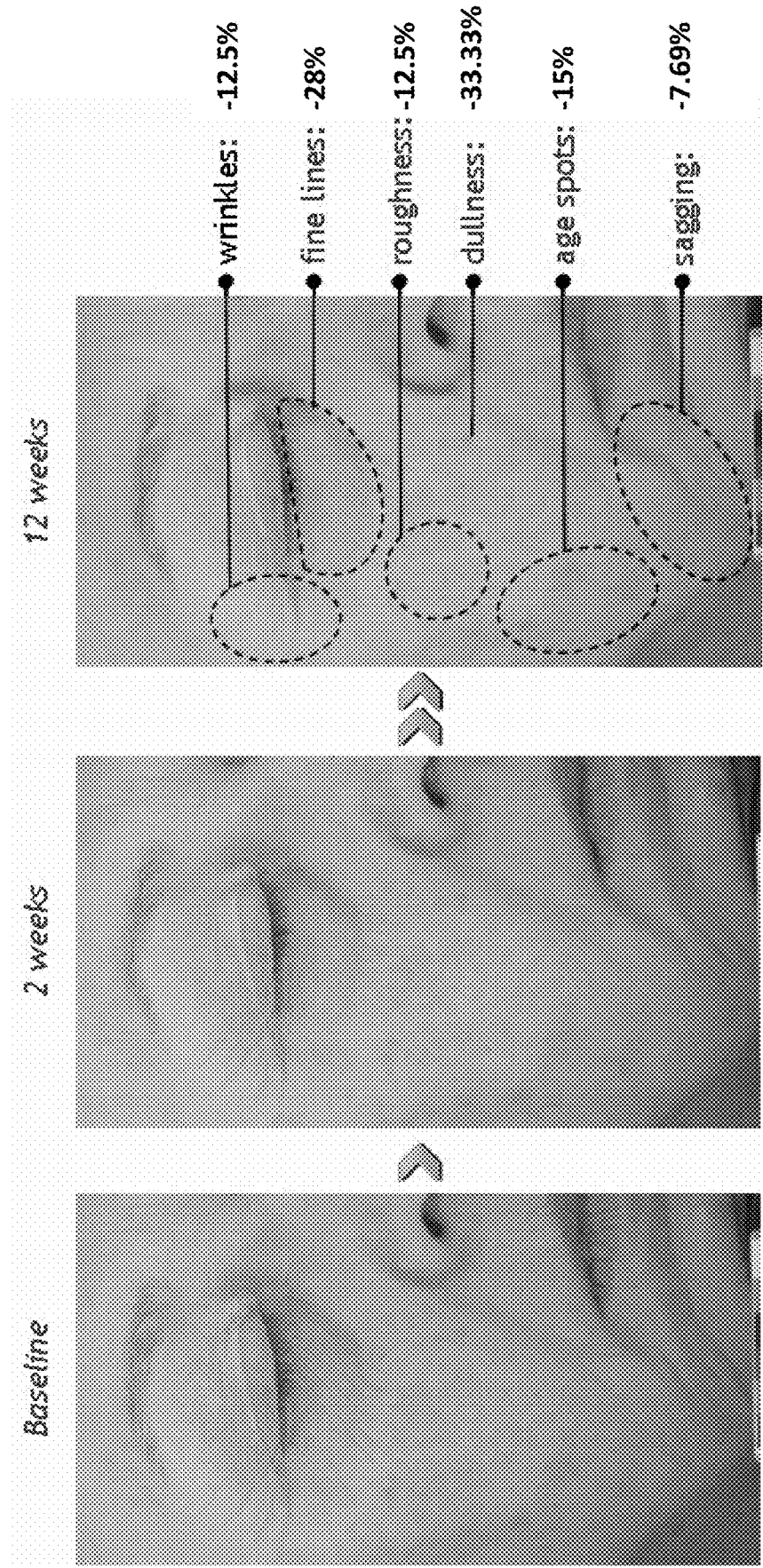

Example 1: Isolation of Leukolectin and Preparations Comprising Leukolectin

Leukolectin proteins (set out below) and methods for providing the same have been described in detail in WO 2010/049688, which is incorporated herein by reference in its entirety. However, for completeness, a preferred method for preparing a composition comprising leukolectin is described below and exemplifies the method described above.

A method for preparing partially purified zonase which may be used as the starting material for isolating the polypeptide of the invention is provided in WO99/29836 which is hereby incorporated by reference (particularly Example 1 of the described method, but optionally without the urea step).

Leukolectin was purified from salmon hatching fluid. To improve the protein concentration of hatching fluid, salmon eggs were transferred to minimal volumes of water prior to hatching. Highly synchronous hatching can be induced by elevated (room) temperatures, or by deoxygenation (Oppen-Berntsen et al. 1990, Aquaculture, 86, pp. 417-430), which yields a small volume of highly concentrated preparation of crude leukolectin and associated proteins. Hatching should be complete within 2 hours for more than 95% of the embryos.

The hatching fluid was filtered using a standard filter with a 7 μm pore size, to remove material likely to clog filters in subsequent filtration steps. This filtrate, the processed hatching fluid, may be frozen for years without significant degradation, before being thawed and employed for further protein purification. This fact greatly simplifies production of a starting material for purifying salmon leukolectin.

The processed hatching fluid was subjected to filtration using a filter with a 0.45 μm pore size and the filtrate was collected. The filtrate was then diafiltrated with a filter exclusion size of 8 kDa to exchange water of hatching fluid for buffer. In this case, the buffer contained 0.5 mM phosphate and 1 mM NaCl, although other buffers are equally suitable. For example, phosphate buffered saline or buffers containing millimolar Tris (e.g. 10 mM) at pH around neutrality or slightly alkaline (pH 7.5-8.5), containing 5 mM NaCl, are suitable. The retentate from the diafiltration step was collected and diluted by the addition of the buffer.

The diafiltrate was subjected to ultrafiltration using ultra filters with size exclusion of 100 kDa and the filtrate comprising the leukolectin was collected. Finally, the filtrate was subjected to filtration through a filter with a pore size of 0.22 μm and the final filtrate was collected. This filtrate is an enriched preparation of leukolectin.

Example 2: In Vitro Activity of Leukolectin on Fibroblasts

Materials and Methods

Compositions prepared according to the method in Example 1 were applied to senescent fibroblasts (Human dermal fibroblasts, replicative of the Hayflick ageing model Hayflick, L., and Moorhead, P. S. (1961). "The serial cultivation of human diploid cell strains." Exp Cell Res 25:585-621). In this respect, senescent fibroblasts release increased amounts of MMPs in comparison to young fibroblasts and, as discussed above, MMP activity is associated both with the signs and symptoms of ageing and scarring. In particular MMP-1, known as interstitial collagenase or fibroblast collagenase, is involved in the breakdown of the extracellular matrix because it cleaves interstitial collagen types I, II and III.

Three different concentrations of the leukolectin composition were applied to senescent fibroblasts, 0.015%, 0.050% and 0.150% [v/v]. The composition is an enriched preparation of leukolectin and the v/v refers to the total volume of the enriched preparation (including non-leukolectin components) per unit volume. The concentration of MMP-1 was measured by ELISA. Two control experiments were performed simultaneously. The first control involved the use of Normal Human Dermal Fibroblasts (NHDF) which were isolated from the dermis of juvenile foreskin or adult skin from different locations like the face, and therefore demonstrate normal "non-ageing" levels of MMP-1 (P7-NHDF). The second control comprises senescent cells that were contacted with TGF-β (10 ng/ml) instead of leukolectin. TGF-β (Transforming growth factor β) is a multifunctional cytokine that regulates cell proliferation and differentiation, tissue modeling and repair. It is known to inhibit the release of MMP-1. The results are shown in Table 2, from which it can be seen that the leukolectin composition at concentrations of 0.050% and 0.150% result in almost complete inhibition of the release of MMP-1 from senescent fibroblasts, such that the levels are below even those of juvenile fibroblasts. These results indicate that leukolectin can be expected to be useful in improving the cosmetic appearance of skin, particularly aged and scarred skin, which show increased levels of MMPs and/or abnormal MMP activity. In fact, the below results, which show the effects of a composition comprising leukolectin confirm the effects of such compositions on aged skin.

The Table key is as follows:
(1): Threshold for statistical significance
ns: >0.05, Not significant
*: 0.01 to 0.05, Significant
**: 0.001 to 0.01, Very significant
***: <0.001, Extremely significant
< or >: Inferior or superior to the detection limit A double blind, placebo controlled clinical trial was conducted to evaluate the effectiveness and tolerance of topical skin treatments in females with mild to moderate photodamaged, i.e. aged, facial skin. The duration of this trial was 12 weeks with visits at baseline, Week 2, Week 6 and Week 12. Efficacy was assessed using visual grading, instrumentation, digital VISIA CR photographs and subject self-assessment questionnaires.

Number of Subjects

One hundred and one (101) female subjects completed participation in the study (N>30 for the three treatments, i.e. one placebo and two compositions comprising the active component, i.e. leukolectin, at different concentrations).

Subject Population and Identification

Subjects were healthy females ages 40 to 65 and were assigned a three-digit number which, when used in conjunction with the clinical study number, uniquely identified every subject in the study. This number remained with the subject throughout the study to maintain the anonymity of the experiment.

TABLE 2

| | | | Basic data | | | | | | Normalized data | | | Viability (MTT) |
|---|---|---|---|---|---|---|---|---|---|---|---|---|
| | | | MMP-1 (ng/ml) | | | | | | | | | |
| Treatment | | | dilution factor adjusted | Mean MMP-1 (ng/ml) | Standard Error (ng/ml) | % Control P17-F | Standard Error (%) | $p^{(1)}$ | Inhibition (%) | Standard Error (%) | $p^{(1)}$ | % Control P17-F |
| Test compound | | Concentration | | | | | | | | | | |
| P7-NHDF (juvenile fibroblasts) | Control (no treatment) | — | 13.9 15.8 16.2 | 15.3 | 0.7 | 32 | 1 | *** | 68 | 1 | *** | 139 |
| P17-F (senescent fibroblasts) | Control (no treatment) | — | 42.8 48.6 51.6 41.9 49.1 51.4 | 47.5 | 1.7 | 100 | 4 | — | 0 | 4 | — | 100 |
| | TGF-β | 10 ng/ml | 41.8 34.3 41.7 42.3 45.2 31.8 | 39.5 | 2.1 | 83 | 5 | * | 17 | 5 | * | 120 |
| | Leukolectin | 0.015% | 49.1 51.9 56.0 | 52.3 | 2.0 | 110 | 4 | ns | −10 | 4 | ns | 133 |
| | | 0.050% | <4.7 <4.7 <4.7 | <4.7 | 0.0 | <10 | 0 | *** | >90 | 0 | *** | 185 |
| | | 0.150% | <4.7 <4.7 <4.7 | <4.7 | 0.0 | <10 | 0 | *** | >90 | 0 | *** | 181 |

Example 3: In Vivo Effects of Leukolectin on Aged Skin

A composition comprising leukolectin was prepared as described in Example 1, however the penultimate step of ultrafiltration through a filter with a 100 kDa exclusion size was omitted. The composition was prepared as a 1% and 3% skin lotion [v/v] (total volume of composition per unit volume of lotion), the two active skin lotions in the trial, and compared to a control skin lotion which did not comprise the active component, i.e. the hatching fluid composition. The skin lotion was an oil in water (O/W) emulsion. The oil phase represents 9% of the total composition and was emulsified with hydrogenated lecithin.

Eligibility Criteria

Inclusion Criteria

1. Females, ages 40 to 65, inclusive, who were in general good health as determined by the health and eligibility questionnaire.

2. Willingness to cooperate and participate by following study requirements for the duration of the study and to report any adverse symptoms immediately 3. Clinically determined mild to moderate photodamage (fine lines, wrinkles, hyperpigmentation, laxity and roughness) on the face corresponding to the modified Griffith's grading scale with scores of 3-7.

4. Free of any disease state or physical facial skin conditions (e.g. atopic dermatitis, eczema, psoriasis, seborrheic dermatitis) which might impair evaluations of the test sites or increase the health risk to the subject by study participation.

5. Willingness to avoid extended periods of sun exposure and all use of tanning beds for the duration of the study. Extra care should be taken to wear protective clothing, including sunglasses, and avoid sun exposure from 10 AM to 4 PM.

6. Willingness to continue use of all regular brands of colour cosmetics, cleanser, toner (if applicable) and makeup remover for the duration of the study. Individuals had to refrain from using any anti-ageing products or skin lightening products other than the assigned test material.

7. Willingness to remove all makeup at least 20 minutes prior to each scheduled clinic visit. No other topical products were to be applied to the face or eye area until the study visit was completed. If a subject arrived having not removed all makeup, she was required to remove the residual makeup at the clinic and wait at least 20 minutes prior to procedures.

8. Individuals who were taking hormone replacement therapies or hormones for birth control had to be on a stable regimen for at least one month prior to the study start and they had to be willing to continue and not change this medication for the duration of the study. Individuals who were not taking HRT or hormones at the start of the study had to be willing to not begin use during the course of the study.

9. Willingness to cooperate and participate by following study requirements and to report any adverse symptoms immediately.

Exclusion Criteria

1. Individuals with a history of intolerance or allergy to any personal care product.

2. Individuals who had used any prescription or OTC skin lightening products less than 30 days prior to the study entry.

3. Individuals who had a condition and/or disease of the skin that the examining Investigator deemed inappropriate for participation.

4. Individuals who were nursing, pregnant, or planning to become pregnant during the study.

5. Individuals who had routinely used any anti-ageing, anti-wrinkle, topical antioxidants, less than 30 days prior to the study entry.

6. Individuals who had used an enzymatic facial skin treatment within 6 months of the study start.

7. Use of Retin-A®, Retin-A Micro®, Renova®, Avita®, Tazorac®, Avage® or Differin® or other topical retinoids within 3 months of the study start, or had taken Accutane or an oral retinoid within the past 6 months.

8. Routine use of products containing alpha-, beta- or poly-hydroxyacid (including salicylic acid and Lachydrin), retinol or derivatives of retinol or other 'anti-ageing' products on the face within 30 days of the study start.

9. Individuals who had received a facial dermabrasion or chemical peel treatment within 3 months of treatment or during the study.

10. Individuals who had received treatment with light RF, or other devices in the treated area within the treated area within 6 months of treatment or during the study.

11. Individuals who had received Botox, collagen, fat injections or other methods of augmentation with injected or implanted material in the treated area within 9 months of treatment or during the study.

12. Individuals who had undergone a resurfacing procedure, face lift or eye or eyelid surgery within 12 months prior to the start of this trial.

13. Individuals who had pre-existing and/or dormant dermatologic conditions on the face (e.g., vitiligo, atopic dermatitis, psoriasis, rosacea, eczema, seborrheic dermatitis, severe excoriations etc.) or medical condition/disease which in the opinion of the Investigator could have interfered with the outcome of the study.

14. Individuals who had a history of immunosuppressant/immune deficiency disorders (including (HIV infection or AIDS) or currently using immunosuppressive medications.

15. Individuals who were participating in any other clinical usage study (patch studies are acceptable).

16. Individuals who had an uncontrolled disease such as diabetes, hypertension, hyperthyroidism or hypothyroidism. Some individuals who had multiple health conditions were excluded from participation even if the conditions are controlled by diet, medication, etc.

17. Individuals who had participated in any clinical trial within 28 days prior to inclusion into the study.

Individuals were admitted to the study at the discretion of the Investigator or his designate based on medical history and findings of the pre-study interview and examination.

Study Design

The double blind, placebo controlled clinical trial was conducted to evaluate the effectiveness of topical skin treatments in females with mild to moderate photodamaged, i.e. aged, facial skin. The duration of this trial was 12 weeks with visits scheduled at baseline, Week 2, Week 6 and Week 12. Efficacy was assessed using visual grading, instrumentation, digital VISIA CR photographs and subject self-assessment questionnaires.

Three groups of N>30 per group completed the study. Subjects received an active skin treatment, namely the leukolectin composition described above, or a vehicle control (water) to apply to the face for twelve weeks. Randomization of subjects into the 3 groups was performed according to a pre-determined randomization.

|  | Visit: | | | |
|---|---|---|---|---|
|  | Visit 1 Baseline | Visit 2 Week 2 | Visit 2 Week 6 | Visit 2 Week 12 |
| Informed Consent, eligibility paperwork, facial screening | X | | | |
| Riant and left side clinical scoring for lines, wrinkles, mottled hyperpigmentation, laxity, clarity and roughness | X | X | X | X |
| Right and left side clinical scoring for objective and subjective irritation (erythema, dryness, burning/stinging*, itching*, tight/dry feeling*) *reported by the panelist. | X | X | X | X |
| Right and left side VISIA-CR imaging | X | X | X | X |
| Cutometer measurements on the right and left face. | X | X | X | X |

|  | Visit: | | | |
|---|---|---|---|---|
|  | Visit 1 Baseline | Visit 2 Week 2 | Visit 2 Week 6 | Visit 2 Week 12 |
| Transepidermal water loss (TEWL) measurements on the right and left face. | X | X | X | X |
| Distribution of test material, vehicle, usage instructions, diary and calendar | X |  | X |  |
| Completion of self assessment questionnaires for right and left face. |  | X | X | X |
| Diary review and product weighing for compliance |  | X | X | X |

Efficacy and Tolerability Evaluations

An expert clinical grader assessed the right and left side of the face for the parameters shown below. A modified Griffith's scale was used, where 0=none, 1-3=mild, 4-6=moderate and 7-9=severe. Half points were used when needed to better describe the skin condition.

Fine Lines
Wrinkles
Hyperpigmentation
Laxity
Dull/Matte (Clarity)
Tactile Roughness An expert clinical grader assessed the right and left side of the face for the parameters shown below. A four point scale was used, where 0=none, 2=mild, 3=moderate and 4=severe. Half points were used when needed to better describe the skin condition.

Erythema
Dryness/scaling
Burning/stinging feeling
Itching
Tight/dry feeling
Digital VISIA CR Photography VISIA-CR imaging was taken of the right and left sides of the face. The subjects were imaged such that their hair was pulled back, jewelry was removed, eyes were closed, the subject was centered within the frame and had a neutral facial expression.

Transepidermal Water Loss (TEWL)

Prior to Instrumental measurements, subjects were made to equilibrate to ambient conditions of the clinic for at least 20 minutes. Ambient conditions were recorded hourly during the study visits. During this time, subjects were graded, completed questionnaires and/or had VISIA CR imaging performed.

The Tewameter was used to take a transepidermal water loss (TEWL) measurement at all visits. Measurements were taken on the right and left cheek at the intersection of lines extending down from the corner of the eye and horizontally across the bottom of the nose.

The Tewameter measures TEWL utilizing an open chamber system. A hand held probe placed on the skin surface sampled relative humidity at two points above the surface, allowing the rate of water loss to be calculated from the measured humidity gradient.

Cutometer MPA 580

All subjects had Cutometer measurements taken at all visits. The Cutometer was used to assess the viscoelastic properties (i.e. extensibility and elasticity) of the skin. The instrument applies a vacuum to a small area of skin and measures the elastic response of the skin (movement of the skin into and out of the aperture) by an optical technique.

For this study, the 2 mm probe was used, a vacuum of 300 mbar was applied and two cycles of suction and release were performed. Cycle times was 5 seconds on and 10 seconds off.

Measurements were taken on the right and left cheek at the intersection of lines extending down from the corner of the eye and horizontally across the bottom of the nose, or an alternate location near the jaw.

Skin Assessment and Self-Assessment Questionnaires

Subjects completed a skin self assessment questionnaire containing questions that describe how the subject perceives their facial skin appearance and condition on the right and left sides of the face.

Results

Fine Lines

Figure 2:
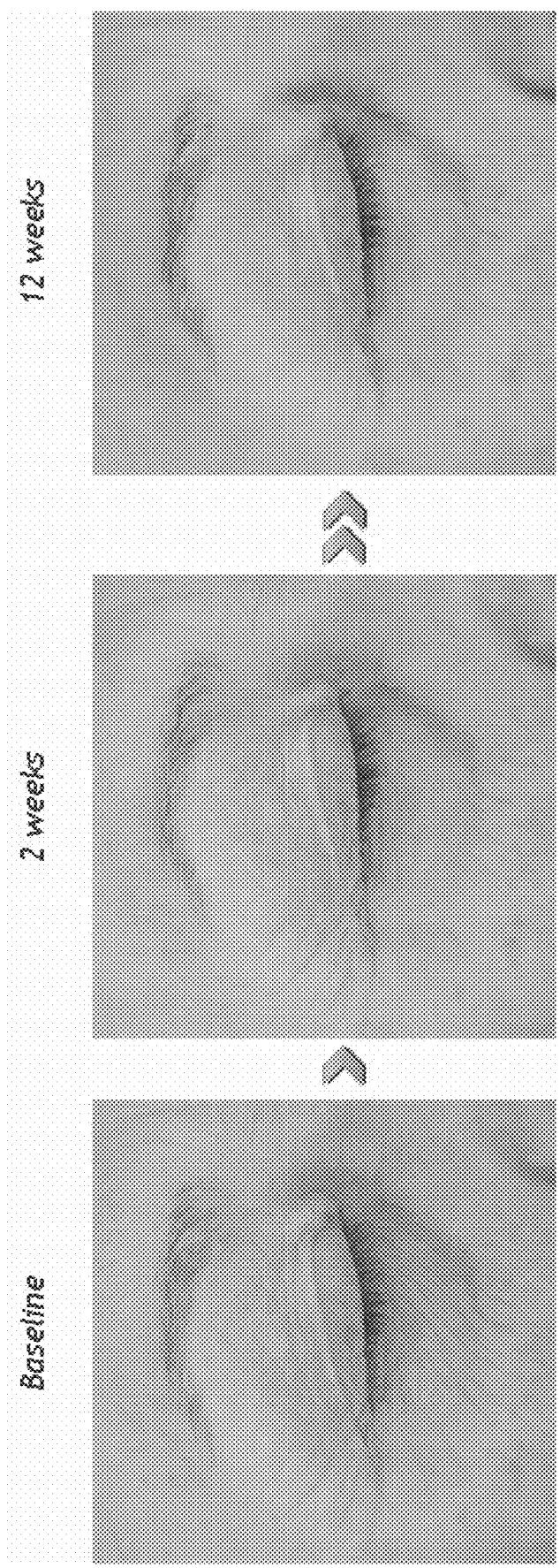
FIG. 2 shows a close-up photograph of the subject in FIG. 1 to emphasise the reduction of fine lines and wrinkles seen after 2 and 12 weeks of treatment with the composition comprising the polypeptide of the invention.

At week 2 subjects treated with a skin lotion comprising one of the active compositions showed a reduction in fine lines (e.g. percentage change of 5.59% (1% solution) and 5.65% (3% solution)) in comparison to the placebo (4.58%). The reduction in fine lines continued at week 6 (e.g. 14.34% (1% solution), 14.86% (3% solution) and 8.98% (placebo)) and week 12 (e.g. 23.43% (1% solution), 25.99% (3% solution) and 14.68% (placebo)). FIGS. 1 and 2 show a subject with a 28% reduction of fine lines.

Wrinkles

Figure 3:
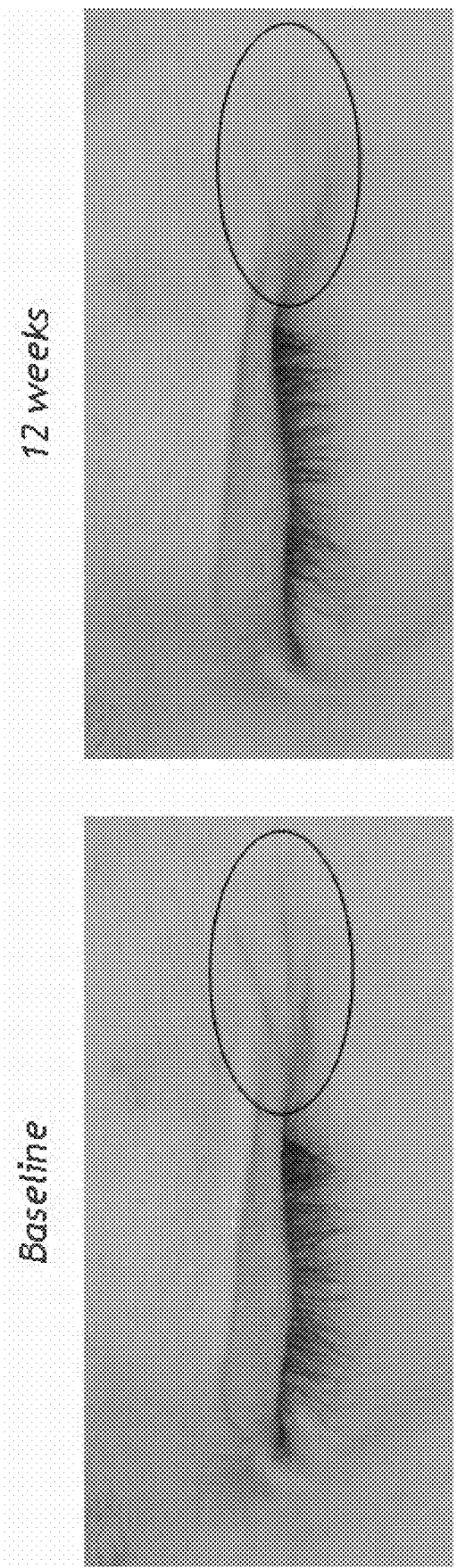
FIG. 3 shows a close-up photograph of a subject treated with the composition comprising the polypeptide of the invention before treatment (Baseline) and after 12 weeks of treatment. The circled area shows a clear reduction of wrinkles after 12 weeks of treatment.

At week 2 subjects treated with a skin lotion comprising one of the active compositions showed a reduction in wrinkles (e.g. percentage change of 2.15% (1% solution) and 1.75% (3% solution)) in comparison to the placebo (0.70%). The reduction in wrinkles continued at week 6 (e.g. 6.13% (1% solution), 7.32% (3% solution) and 3.70% (placebo)) and week 12 (e.g. 14.72% (1% solution), 15.15% (3% solution) and 9.57% (placebo)). FIG. 1 shows a subject with a 12.5% reduction in wrinkles. FIG. 3 shows a subject with a 26.32% reduction in wrinkles.

Hyperpigmentation

At week 2 subjects treated with a skin lotion comprising one of the active compositions showed a reduction in hyperpigmentation (e.g. percentage change of 2.11% (1% solution) and 2.68% (3% solution)) in comparison to the placebo (0.40%). The reduction in hyperpigmentation continued at week 6 (e.g. 5.61% (1% solution), 7.91% (3% solution) and 3.16% (placebo)) and week 12 (e.g. 10.53% (1% solution), 15.35% (3% solution) and 5.73% (placebo)). FIG. 1 shows a subject with an 15% reduction in the pigmentation of an age spot after 12 weeks.

Laxity

At week 2 subjects treated with a skin lotion comprising one of the active compositions showed a reduction in laxity (e.g. percentage change of 2.64% (1% solution) and 1.62% (3% solution)) in comparison to the placebo (0.87%). The reduction in laxity continued at week 6 (e.g. 6.33% (1% solution) and 6.61% (3% solution), 2.51% (placebo)) and week 12 (e.g. 10.55% (1% solution) and 11.33% (3% solution), 5.18% (placebo)). FIG. 1 shows a subject with an 7.69% reduction in laxity (sagging) after 12 weeks.

Dull/Matte (Clarity)

At week 2 subjects treated with a skin lotion comprising one of the active compositions showed an improvement in skin clarity (e.g. percentage change of 12.95% (1% solution) and 16.00% (3% solution)) in comparison to the placebo (10.67%). The improvement continued at week 6 (e.g. 29.26% (1% solution), 28.50% (3% solution) and 19.07% (placebo)) and week 12 (e.g. 37.17% (1% solution), 39.18% (3% solution) and 26.72% (placebo)). FIG. 1 shows a subject with a 33.33% reduction in dullness.

Tactile Roughness

At week 2 subjects treated with a skin lotion comprising one of the active compositions showed a reduction in the tactile roughness of the skin (e.g. percentage change of 16.51% (1% solution) and 20.24% (3% solution)) in comparison to the placebo (13.38%). The improvement continued at week 6 (e.g. 24.77% (1% solution), 26.65% (3% solution) and 16.79% (placebo)), but there was not a further reduction at week 12 (e.g. 26.61% (1% solution), 29.19% (3% solution), and 15.79% (placebo)). FIG. 1 shows a subject with a 12.5% reduction in tactile roughness.

Dryness/Scaling

At week 2 subjects treated with a skin lotion comprising one of the active compositions showed a reduction in the dryness/scaling of the skin (e.g. percentage change of 72.09% (1% solution) and 100.00% (3% solution)) in comparison to the placebo (64.71%). However, at week 6 (e.g. 86.05% (1% solution), 84.62% (3% solution) and 100.00% (placebo)), and week 12 there was not a further reduction when compared to the placebo (e.g. 90.70% (1% solution), 100.00% (3% solution) and 89.47% (placebo)).

TEWL

Whilst subjects treated with a skin lotion comprising one of the active compositions showed a reduction in TEWL at week 2, this was not clearly different to the placebo (e.g. percentage change of 15.35% (1% solution) and 14.53% (3% solution)) in comparison to the placebo (17.26%). However, at week 6 (e.g. 29.46% (1% solution), 26.66% (3% solution) and 22.96% (placebo)), and week 12 there was a further reduction greater than that of the placebo (e.g. 37.46% (1% solution), 40.04% (3% solution), and 34.21% (placebo)).

Extensibility

Whilst subjects treated with a skin lotion comprising one of the active compositions showed an improvement in the extensibility of the skin at week 2, this was only slightly different to the placebo (e.g. percentage change of 16.18% (1% solution) and 17.21% (3% solution)) in comparison to the placebo (10.82%). At week 6 there was no clear difference between the three treatments (e.g. 18.04% (1% solution), 17.18% (3% solution) and 19.90% (placebo)), but at week 12 there was a further improvement for the skin treatment with the compositions comprising the active component, which was greater than that of the placebo (e.g. 31.84% (1% solution), 33.57% (3% solution), and 16.48% (placebo)).

Figure 4:
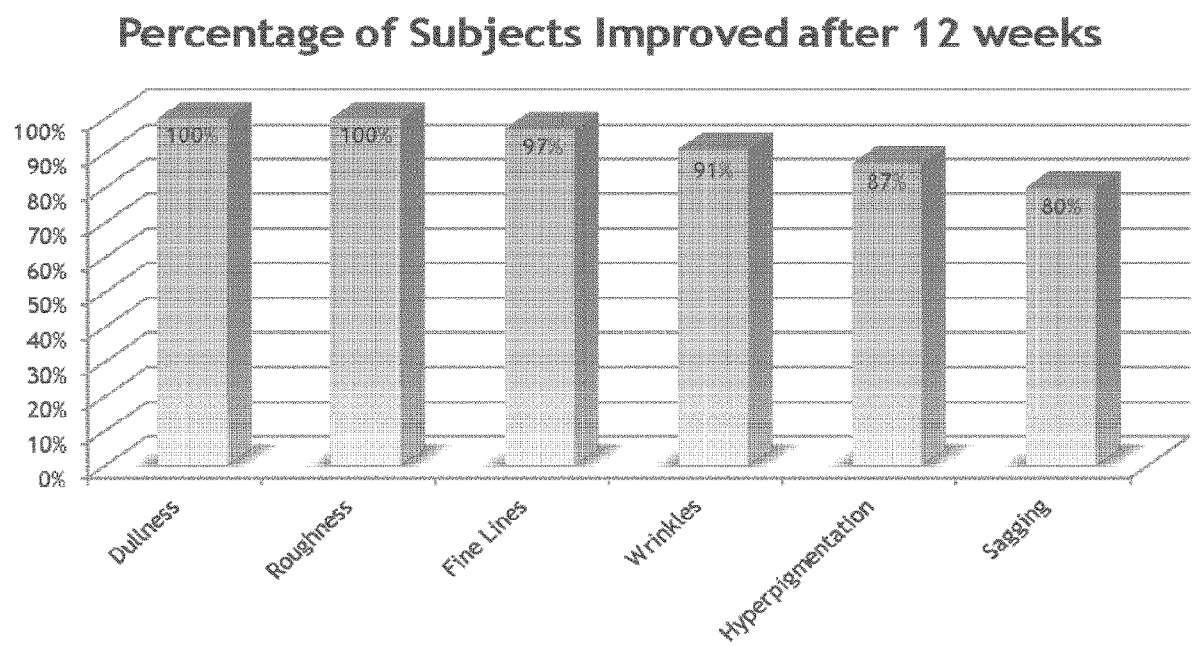
FIG. 4 shows a bar chart depicting the percentage of subjects that were considered to have improved in various signs of ageing based on a tactile/visual clinical grading on both sides of the face.

A comparison of the tactile/visual clinical grading on both sides of the face performed at the start of the study (baseline) and after 12 weeks of treatment shows that the all of the subjects showed improvements in the dullness and roughness of their skin following treatment with the composition comprising the polypeptide of the invention and the majority of subject showed improvements in fine lines (97% of subjects), wrinkles (91% of subjects), hyperpigmentation (87% of subjects) and sagging (80% of subjects) (FIG. 4).

Questionnaires reveal that from 6 weeks of use statistically significant differences were found for mean scores of statements about overall appearance, overall feel, smoothness, softness, clarity and elasticity between the placebo and the cosmetic composition comprising the polypeptide of the invention.

Thus, it is evident from the above results that the composition comprising the leukolectin demonstrated an effect on each aspect of aged skin in comparison to the placebo.

Example 4: Alternative Method for Production of a Leukolectin Containing Composition The initial steps of the alternative method of production of a leukolectin containing composition are the same as those described in Example 1. However, the alternative production method diverges from the method of Example 1 after the hatching fluid is filtered using a standard filter with a 7 µm pore size, to remove material likely to clog filters in subsequent filtration steps. In the alternative method this filtrate, the processed hatching fluid, was loaded on to a diethylaminoethyl (DEAE) ion exchange column according to the manufacturer's instructions and washed with a solution of 20 mM Tris HCl (pH 8.50). The flowthrough was discarded. The leukolectin protein was eluted from the column with the wash solution containing 50 mM NaCl. The eluate was collected and then diafiltrated with a filter exclusion size of 8 kDa to exchange the water of the hatching fluid for buffer. In this case, the buffer was phosphate buffered saline, although other buffers are equally suitable. For example, buffer containing 0.5 mM phosphate and 1 mM NaCl or buffers containing millimolar Tris (e.g. 10 mM) at pH around neutrality or slightly alkaline (pH 7.5-8.5), containing 5 mM NaCl, are suitable. The retentate from the diafiltration step was collected and diluted by the addition of the buffer.

Finally, the filtrate was subjected to filtration through a filter with a pore size of 0.22 µm and the final filtrate was collected. This filtrate is a highly enriched preparation of leukolectin, comprising no or only trace amounts of peptides from the hatching fluid.

Example 5: In Vivo of Leukolectin Composition on Aged Skin

Objective of the Study

The objective of this double blinded skin care study was to evaluate the alterations regarding the skin hydration and the transepidermal water loss (TEWL) on the forearms after a 3 week treatment regimen with a gel comprising 3% of the leukolectin preparation of Example 4 in relation to the untreated situation. Moreover, the influence of leukolectin on the pigmentation of age spots on the hands (melanin content) and the volume of selected eye wrinkles was analysed in relation to the untreated situation.

Material and Methods

The study was carried out according to the SOP "Hautpflege-Prufung Standard", version 4 from 29 Jan. 2003 with modifications in the measurement time points.

The study was conducted double blinded on 4 female subjects. The subjects were qualified to participate in the study by having dry skin on the forearms (baseline corneometry values <20), eye wrinkles at the lateral canthus and age spots on both hands. All 4 subjects finished the study correctly and completely. The results of all 4 subjects were included in the data analysis. The 4 subjects were of ages between 56.3 and 70.9 years (on average 64.3±6.3 years).

The test sites to analyse skin hydration and transepidermal water loss (TEWL) were both forearms. There were four test areas on the forearms, namely two on each inside of the forearm. Two areas were treated with the gel comprising the leukolectin preparation, one was treated with glycerine (control) and the fourth was left untreated. Allocation of treatments to the test areas was permutated.

The test sites for the eye wrinkle measurements were the wrinkle area around the right and left eye (lateral canthus). One side was treated the gel comprising the leukolectin preparation, as randomised, whereas the other side was left untreated.

The effect of the gel comprising the leukolectin preparation on the pigmentation was analysed on one selected age spot on each hand. Also, one hand was treated with the gel on the back, as randomised, whereas the other hand was left untreated.

Before the start of the measurements and the treatment there was a preconditioning period of 7 days. Within this period and during the entire period of the study, the use of skin care products, sun screen products, oily or moisturizing skin cleansing products and dermatological therapeutics was not allowed on the forearms, at the lateral canthus of both eyes and the back of both hands. In addition, it was prohibited to intensively expose the test sites to UV light (sun or solarium). On the study days in the institute, the use of make-up was prohibited.

The treatments were performed twice a day by the subjects at home over a period of three weeks. The products were applied at a quantity of about 2 mg/cm$^2$ to the corresponding forearm test site (as randomised, with one test site left untreated and another treated with glycerine as control). Moreover, the gel comprising the leukolectin preparation was applied to the lateral canthus of one side of the face and the back of one hand (left or right—as randomised), with the other side left untreated.

Before starting the first product application (t0) and after three weeks of treatment (t1) the following parameters were measured: skin hydration on the forearm (Corneometer CM825®, 10 repeated measurements); transepidermal water loss on the forearm (TEWL, DermaLab®, 3 repeated measurements); pigmentation of age spots on the dorsa of the hands (Siascope®, 1 measurement, melanin content); and in vivo measurement of the volume of one selected eye wrinkle at the lateral canthus using the 3D in vivo skin measuring system PRIMOS® Pico (3 repeated measurements, wrinkle volume in mm$^3$ computed by means of a generated height image).

The subjects' compliance regarding the correct product application was checked after one week of product treatment.

All measurements were performed in a climate controlled room at 21.5° C. (±1° C.) and 50% (±5%) relative humidity after the subjects had adapted with their uncovered test areas to these indoor climate conditions for at least 30 min. The measurements and treatments at point in time t1 occurred 10-20 hours after the last product treatment.

Figure 5:
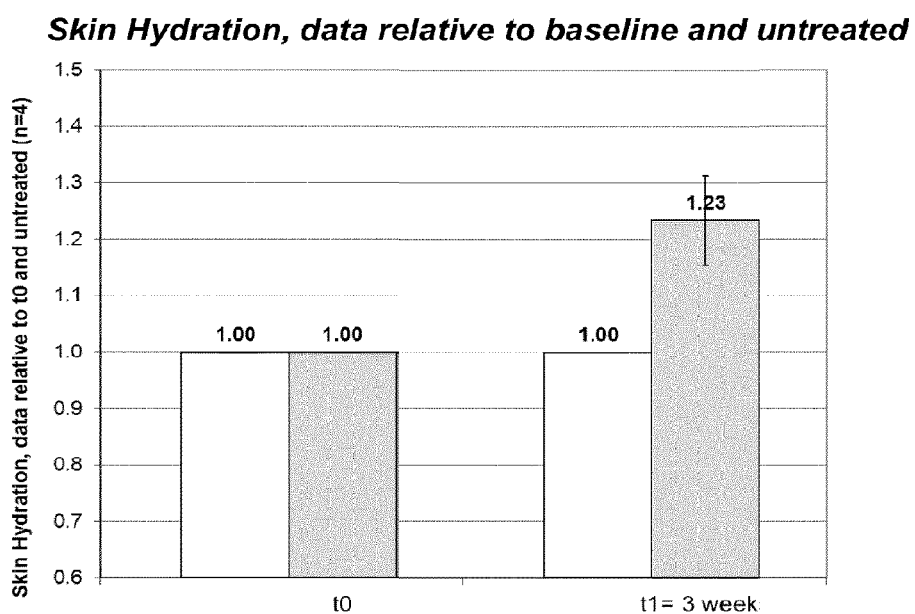
FIG. 5 shows a bar chart depicting the mean increase in skin hydration of about 23% based on 4 subjects compared to the untreated situation after 3 weeks of a twice daily treatment with a composition comprising the polypeptide of the invention.

Drop Outs
There was no drop out.
Discomfort Adverse Skin Reactions
There were no discomfort adverse reactions.
Results The skin treated with the gel comprising 3% v/v of the leukolectin preparation showed an increase in skin hydration in the mean on 4 subjects of about 23% compared to the untreated situation after 3 weeks of a twice daily product treatment (FIG. 5).

Figure 6:
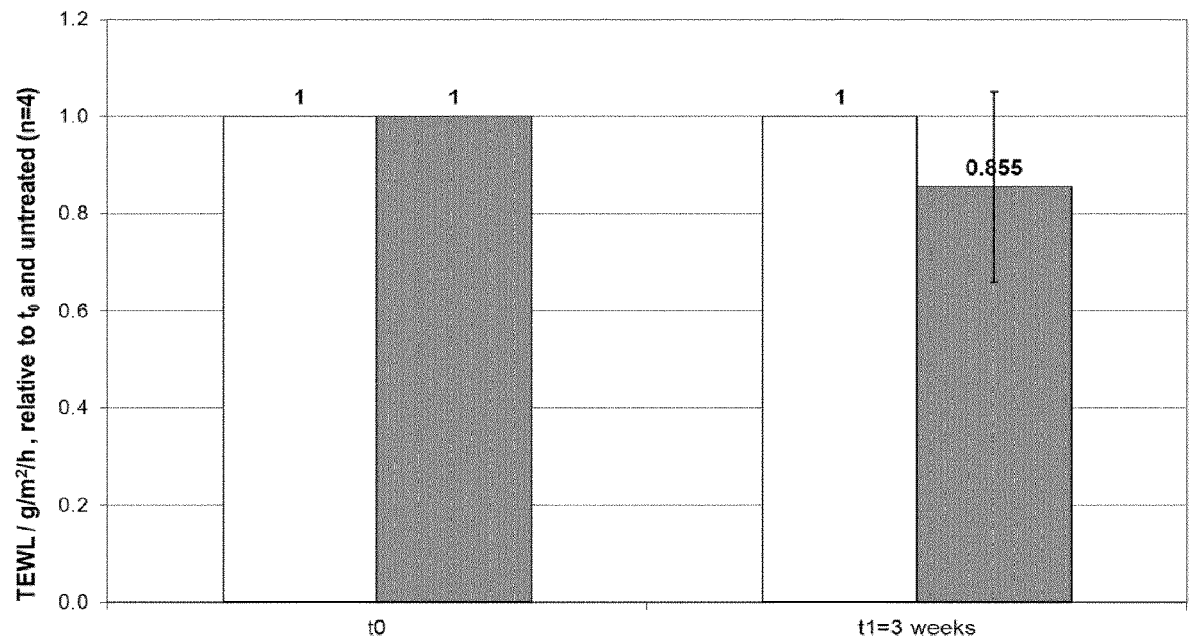
FIG. 6 shows a bar chart depicting the mean decrease in transepidermal water loss (improved skin barrier function) of about 14.5% based on 4 subjects compared to the untreated situation after 3 weeks of a twice daily treatment with a composition comprising the polypeptide of the invention.

The skin treated with the gel showed a decrease in the transepidermal water loss (improvement in skin barrier function) in the mean on 4 subjects of about 14.5% compared to the untreated test site after 3 weeks of a twice daily treatment (FIG. 6).

Figure 7:
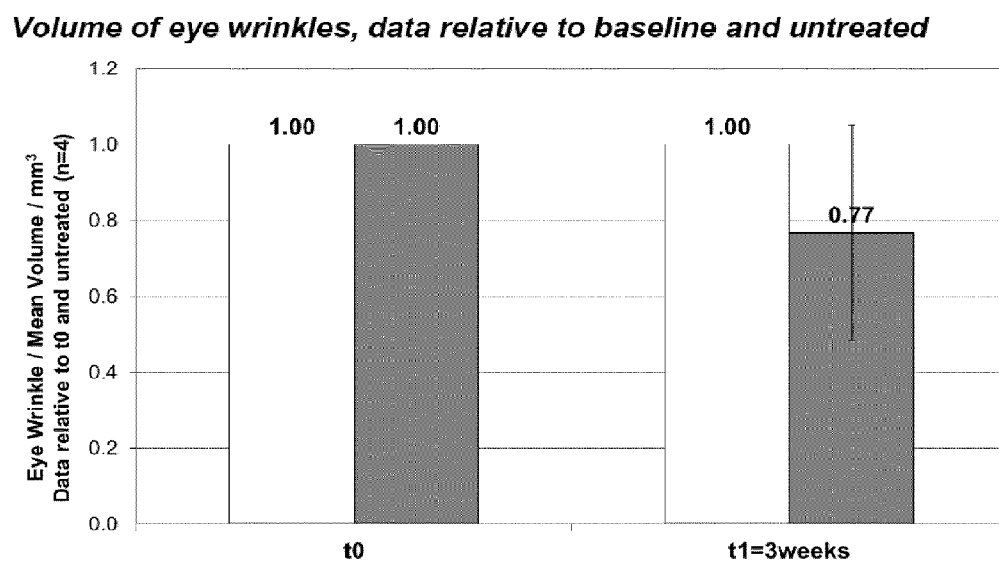
FIG. 7 shows a bar chart depicting the mean decrease in eye wrinkle volume of about 23% based on 4 subjects compared to the untreated situation after 3 weeks of a twice daily treatment with a composition comprising the polypeptide of the invention.

The skin treated with the gel showed a decrease in the eye wrinkle volume of about 23% compared to the untreated test site after 3 weeks of a twice daily treatment (FIG. 7).

Figure 8:
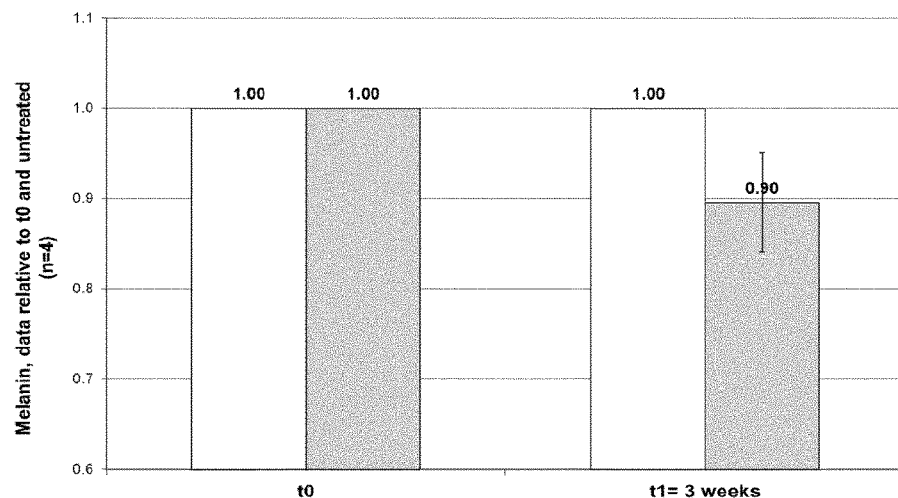
FIG. 8 shows a bar chart depicting the mean decrease in melanin content of about 10% based on 4 subjects compared to the untreated situation after 3 weeks of a twice daily treatment with a composition comprising the polypeptide of the invention.

The age spots treated with the gel showed a decrease in pigmentation (melanin content) in the mean on 4 subjects of about 10.0% compared to the untreated test site after 3 weeks of a twice daily treatment (FIG. 8).

Sequences:

1. leukolectin polypeptide from salmon embryo:
MRTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGEQFIVGANMNDTPYCLTSSATVGYKGPGSPLPWTGLPGAVKYYS
CGPFGCWAVNKNDDIYLMSLNQDCQNKGWSHIEGKLSMIEVATDGSVFGV
NSAGSVYTRDGITASKPEGTGWSNIPMGMLMGHVTYDLGRLWVVSKSAVT
MVCTH 2. leukolectin polypeptide from salmon leukocytes:
SIPYYLVGDKWIRLPGSLKHITVGPAGIWGVNKDYAIYKYVAGNWVQAAG
LPKQLDAGGEQFIVGANMDDTPYCLTSSATVGYKGPGSPLPWTGLPGAVK
YYSCGPFGCWAVNKNDDIYLMSLNQDCQNNGWSHIEGKLSMIEVATDGSV
FGVNSAGSVYTRDGITASKPEGTGWSNIPMCMLMGHVTYDLGRLWVVSKS
AVTMVCTH 3. leukolectin-2 polypeptide from salmon:
MRTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGNQFVVGANMDDTPFCLTSSATVGYKGPGSPLPWTGLPGAVKYYS
CGHFGCWAVNKNDDIFLMSLNQDCQNNGWSHIDGKLSMIEVATDGSVFGV
NSAGSVYTRDGITASKPEGTGWSNIPMGMLMGHVTYDLGRLWVVSKSGGT
MVCTH 4. leukolectin-3 polypeptide from salmon:
MGTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGEQFIVGANMNDTPYCLTSSATVGYKGPGSPLPWTGLPGAVKYYS
CGPFGCWAVNKNDDIYLMSLNQDCQNKGWSHIEGKLSMIEVATDGSVFGV
NSAGSVYTRDGITASKPEGTGWSNIPMGMLMGHVTYDLGRLWVVYKSAVT
MVCTH

The invention claimed is:

1. A method for improving the cosmetic appearance of a scar in the skin of a mammalian animal, said method comprising administering topically to said scar an effective amount of a cosmetic composition comprising
(i) a polypeptide comprising:
(a) an amino acid sequence as set forth in any one of SEQ ID NOS: 1-4 or a sequence which is at least 90% identical to said sequence; or
(b) a portion of any of said sequences comprising at least 100 contiguous amino acids of said sequence; and
(ii) one or more pharmaceutically acceptable excipients and/or diluents, thereby improving the cosmetic appearance of a scar in the skin of a mammalian animal.

2. The method of claim 1, wherein improving the cosmetic appearance of the scar comprises reducing scar tissue.

3. The method of claim 1, wherein improving the cosmetic appearance of the scar comprises improving the tensile strength of the skin at and around the site of the scar.

4. The method of claim 1, wherein the scar is as a result of a wound.

5. The method of claim 1, wherein the scar is an acne scar.

6. The method of claim 1, wherein the scar is as a result of striae.

7. The method of claim 6, wherein the striae is striae atrophicae, striae vergetures, striae distensae, striae cutis distensae, striae gravidarum, lineae atrophicae or linea albicante.

8. The method of claim 1, wherein the scar is at the proliferation stage of skin healing.

9. The method of claim 1, wherein the scar is at the maturation stage of skin healing.

10. The method of claim 1, wherein said polypeptide has been purified to a degree of purity of more than 95% w/w.

11. The method of claim 1, wherein the composition comprises less than 0.1% w/w of other polypeptides that are present in salmon egg hatching fluid.

12. The method of claim 1, wherein said polypeptide or composition is obtained or obtainable by a method comprising at least the steps of:
a) suspending salmon eggs in water;
b) inducing synchronized hatching of said eggs;
c) filtering the hatched eggs to obtain hatching fluid; and
d) filtering the hatching fluid to obtain the polypeptide and/or composition, wherein the step of filtering the hatching fluid comprises at least the steps of:
(i) filtering the hatching fluid using a filter with a pore size of at least 5 µm, and collecting the filtrate;
(ii) filtering the filtrate from step (i) using a filter with a pore size of 0.30-0.60 µm, and collecting the filtrate;
(iii) exchanging water in the filtrate from step (ii) with a pharmaceutically acceptable buffer to obtain a filtrate solution;
(iv) filtering the filtrate solution obtained from step (iii) using a filter with an exclusion size of at least 80 kDa, and collecting the filtrate; and (v) filtering the filtrate from step (iv) using a filter with a pore size of 0.15-0.30 μm, and collecting the filtrate, wherein said filtrate provides a composition comprising said polypeptide.

13. The method of claim 1, wherein said polypeptide or composition is obtained or obtainable by a method comprising at least the steps of:
a') suspending salmon eggs in water;
b') inducing synchronized hatching of said eggs;
c') filtering the hatched eggs to obtain hatching fluid; and
d') filtering the hatching fluid to obtain the polypeptide and/or composition, wherein the step of filtering the hatching fluid comprises at least the steps of:
(i') filtering the hatching fluid using a filter with a pore size of at least 5 m and collecting the filtrate;
(ii') subjecting the filtrate from step (i') to ion exchange chromatography and collecting the eluate;
(iii') exchanging water in the eluate from step (ii') with a pharmaceutically acceptable buffer to obtain an eluate solution; and
(iv') filtering the eluate solution obtained from step (iii') using a filter with a pore size of 0.15-0.30 μm and collecting the filtrate, wherein said filtrate provides a composition comprising said polypeptide.

14. The method of claim 13, comprising an additional step of filtering the filtrate from step (i') using a filter with a pore size of 0.30-0.60 μm and collecting the filtrate.

15. The method of claim 13, wherein step (ii') comprises:
(a) loading the filtrate on to an ion exchange column;
(b) washing the column with a buffer;
(c) eluting the polypeptide from the column using an elution buffer or solvent; and
(d) collecting the eluate from step (c).

16. The method of claim 12, wherein:
a) the pore size of the filter in step (i) is 5-15 μm;
b) the pore size of the filter in step (ii) is 0.35-0.55 μm;
c) the exclusion size of the filter in step (iv) is 80-120 kDa; and/or
d) the pore size of the filter in step (v) is 0.22 μm.

17. The method of claim 13, wherein:
a) the pore size of the filter in step (i') is 5-15 μm; and/or
b) the pore size of the filter in step (iv') is 0.22 μm.

18. The method of claim 12, wherein step (iii) comprises diafiltration.

19. The method of claim 13, wherein step (iii') comprises diafiltration.

20. The method of claim 15, wherein said ion exchange column is a DEAE (diethylaminoethyl) column.

\* \* \* \* \*